United States Patent
Park et al.

(10) Patent No.: US 8,049,872 B2
(45) Date of Patent: Nov. 1, 2011

(54) ENDPOINT DETECTION DEVICE FOR REALIZING REAL-TIME CONTROL OF PLASMA REACTOR, PLASMA REACTOR WITH ENDPOINT DETECTION DEVICE, AND ENDPOINT DETECTION METHOD

(75) Inventors: Kun Joo Park, Gyeonggi-do (KR);
Kwang Hoon Han, Gyeonggi-do (KR);
Kee Hyun Kim, Gyeonggi-do (KR);
Weon Mook Lee, Gyeonggi-do (KR);
Kyounghoon Han, Seoul (KR);
Heeyeop Chae, Gyeonggi-do (KR)

(73) Assignee: DMS Co., Ltd., Suwon, Kyungki-Do (KR)

( * ) Notice: Subject to any disclaimer, the term of this patent is extended or adjusted under 35 U.S.C. 154(b) by 920 days.

(21) Appl. No.: 12/036,781

(22) Filed: Feb. 25, 2008

(65) Prior Publication Data
US 2009/0029489 A1 Jan. 29, 2009

(30) Foreign Application Priority Data
Jul. 24, 2007 (KR) .................. 10-2007-0073864

(51) Int. Cl.
*G01N 21/00* (2006.01)
(52) U.S. Cl. .................................... 356/72; 156/345.25
(58) Field of Classification Search .................. 356/72; 156/345.24–345.25
See application file for complete search history.

(56) References Cited

U.S. PATENT DOCUMENTS

| | | | |
|---|---|---|---|
| 6,368,975 B1 * | 4/2002 | Balasubramhanya et al. | 438/706 |
| 7,257,457 B2 * | 8/2007 | Imai et al. | 700/121 |
| 7,263,463 B2 * | 8/2007 | Yamazaki | 702/182 |
| 2003/0136511 A1 * | 7/2003 | Balasubramhanya et al. | 156/345.25 |
| 2003/0223055 A1 * | 12/2003 | Agarwal et al. | 356/72 |
| 2005/0055175 A1 * | 3/2005 | Jahns et al. | 702/182 |
| 2005/0143952 A1 * | 6/2005 | Tomoyasu et al. | 702/181 |
| 2005/0146709 A1 * | 7/2005 | Oh et al. | 356/72 |
| 2006/0000799 A1 * | 1/2006 | Doh et al. | 156/345.24 |

FOREIGN PATENT DOCUMENTS

| KR | 20020027634 A | 4/2002 |
|---|---|---|
| KR | 20030006812 A | 1/2003 |

* cited by examiner

*Primary Examiner* — Kara E Geisel
(74) *Attorney, Agent, or Firm* — Volpe and Koenig, P.C.

(57) ABSTRACT

An endpoint detection device, a plasma reactor with the endpoint detection device, and an endpoint detection method are provided. The endpoint detection device includes an OES data operation unit, a data selector, a product generator, an SVM, and an endpoint determiner. The OES data operation unit processes reference OES data by normalization and PCA. The data selector selects part of the linear reference loading vectors and selects part of the selected linear reference loading vectors. The product generator outputs at least one reference product value. The SVM performs regression and outputs a prediction product value. The endpoint determiner detects a process wafer etch or deposition endpoint and outputs a detection signal.

19 Claims, 13 Drawing Sheets

Fig 1a_Prior Art
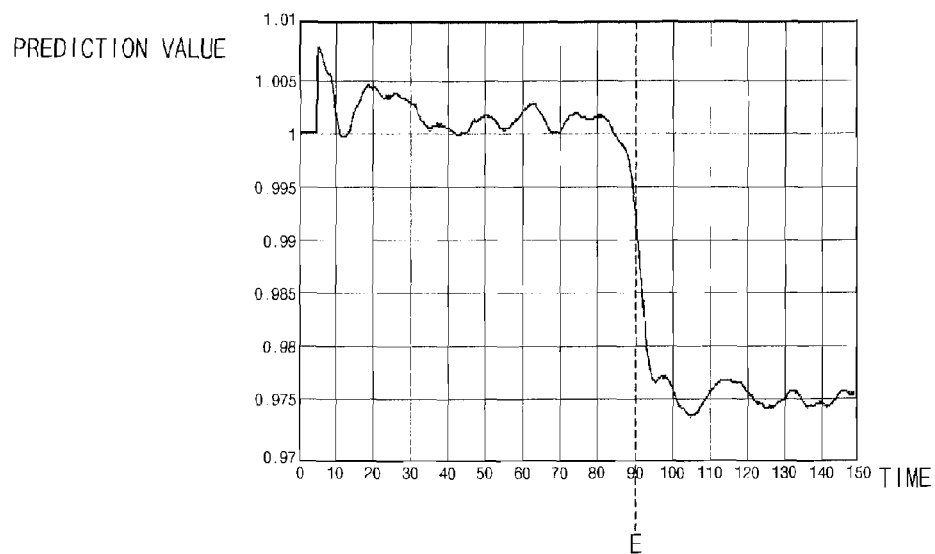
Fig 1b_Prior Art
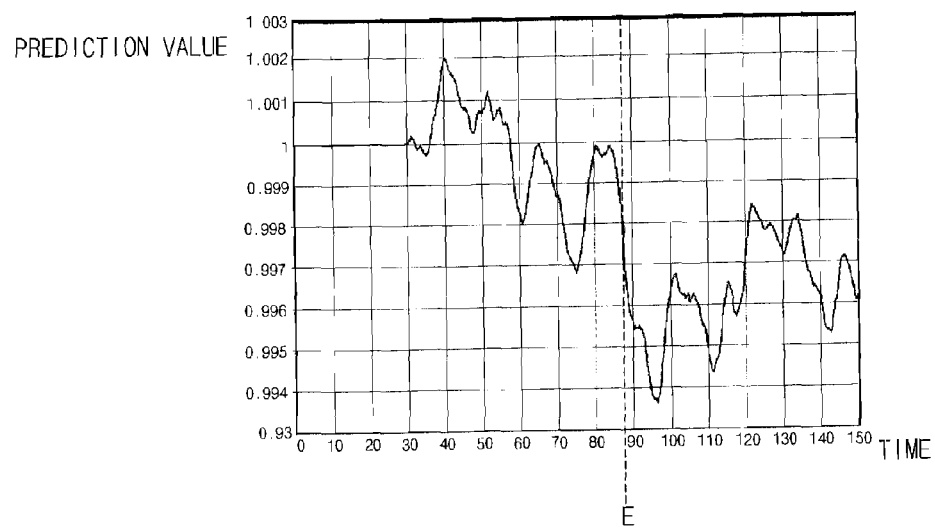

Fig 1c_Prior Art
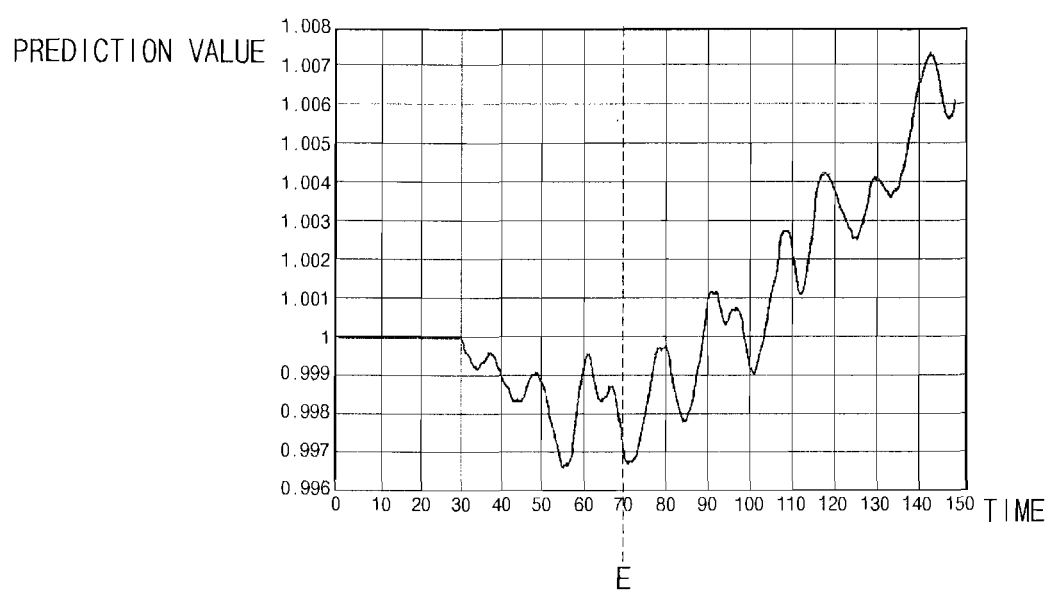

| OES DATA VALUE AT EACH WAVELENGTH | WAVELENGTH INTENSITY VALUE AT EACH TIME ZONE | | | | | |
|---|---|---|---|---|---|---|
| | t1 | t2 | t3 | t4 | t5 | |
| 196.1695 | 18.16667 | 22.25 | 6.333333 | 22 | 26 | |
| 196.4376 | 54.55556 | 46.33333 | 26.77778 | 61 | 67 | |
| 196.7056 | 81.01852 | 59.36111 | 57.59259 | 85.33334 | 76 | |
| 196.9737 | 70.17284 | 47.37037 | 58.8642 | 75.44444 | 60.33333 | |
| 197.2417 | 67.55761 | 39.70679 | 51.28807 | 65.48148 | 72.77778 | |
| 197.5098 | 66.68587 | 39.81893 | 59.09602 | 56.82716 | 84.92593 | |
| 197.7778 | 59.39529 | 47.85631 | 61.69867 | 50.27572 | 80.30864 | |
| 198.0458 | 56.63176 | 57.53544 | 53.56622 | 52.09191 | 72.43621 | |
| 198.3138 | 56.71059 | 71.09515 | 48.18874 | 51.03064 | 71.1454 | |
| 198.5818 | 63.07019 | 64.94838 | 44.06291 | 43.34354 | 59.3818 | |
| 198.8498 | 52.5234 | 35.56613 | 32.68764 | 34.11451 | 47.79393 | |
| 199.1178 | 71.0078 | 59.43871 | 60.22921 | 68.70484 | 66.59798 | |
| 199.3858 | 79.83593 | 86.39623 | 71.40974 | 82.90161 | 74.53266 | |
| 199.6538 | 63.44531 | 81.04874 | 56.80325 | 75.9672 | 73.84422 | |
| 199.9217 | 70.3151 | 78.26625 | 65.93442 | 84.98907 | 89.94807 | |
| ......... | | | | | | |

$$X = \begin{Bmatrix} \overbrace{x1 \ x2 \ x3}^{\text{WAVELENGTH}} \\ 60 \ 58 \ 25 \\ 35 \ 40 \ 75 \\ 74 \ 68 \ 50 \\ 30 \ 40 \ 60 \\ 80 \ 70 \ 50 \\ 90 \ 95 \ 80 \\ 50 \ 50 \ 45 \end{Bmatrix} \begin{matrix} t1 \\ t2 \\ t3 \\ t4 \\ t5 \\ t6 \\ t7 \end{matrix} \xrightarrow[\text{TIME}]{\text{NORMALIZATION SAMPLING}} X' = \begin{Bmatrix} 0.0063 & -0.1096 & -1.6036 \\ -1.0899 & -1.0304 & 1.0690 \\ 0.6201 & 0.4019 & -0.2673 \\ -1.3091 & -1.0304 & 0.2673 \\ 0.8832 & 0.5042 & -0.2673 \\ 1.3217 & 1.7831 & 1.3363 \\ -0.4322 & -0.5189 & -0.5345 \end{Bmatrix}$$

$$D = \text{cov}(X)^* \text{cov}(X)^T \qquad \text{cov}(X) = \begin{Bmatrix} 1.0000 & 0.9578 & 0.0117 \\ 0.9578 & 1.0000 & 0.2028 \\ 0.0117 & 0.2028 & 1.0000 \end{Bmatrix}$$

$$\text{Ve} = \begin{Bmatrix} \overbrace{0.6925}^{A3} & \overbrace{0.2071}^{A2} & \overbrace{0.6910}^{A1} \\ -0.7079 & 0.0109 & 0.7062 \\ 0.1387 & -0.9783 & 0.1541 \end{Bmatrix}$$

$$D = \begin{Bmatrix} 1.9175 & 1.9180 & 0.2167 \\ 1.9180 & 1.9585 & 0.4168 \\ 0.2176 & 0.4168 & 1.0413 \end{Bmatrix}$$

$$\lambda e = \begin{Bmatrix} 0.0005 & 0 & 0 \\ 0 & 0.9905 & 0 \\ 0 & 0 & 3.9262 \end{Bmatrix}$$

$$P = \begin{Bmatrix} \overbrace{0.0223}^{PC3} & 0 & 0 \\ 0 & \overbrace{0.9952}^{PC2} & 0 \\ 0 & 0 & \underbrace{1.9815}_{PC1} \end{Bmatrix}$$

ENDPOINT DETECTION DEVICE FOR REALIZING REAL-TIME CONTROL OF PLASMA REACTOR, PLASMA REACTOR WITH ENDPOINT DETECTION DEVICE, AND ENDPOINT DETECTION METHOD

BACKGROUND OF THE INVENTION

1. Field of the Invention

The present invention relates to a device used in a semiconductor manufacturing process. More particularly, the present invention relates to an endpoint detection device for detecting an etch endpoint or a deposition endpoint during a semiconductor etch or deposition process, a plasma reactor with the endpoint detection device, and an endpoint detection method.

2. Description of the Related Art

In general, until to finish one semiconductor product from a wafer, a series of very complex semiconductor processes are required. A variety of semiconductor processing equipments each are used in a series of semiconductor processes. Operation performance (that is, process conditions) of the semiconductor processing equipments each is a factor of determining operation performance of finished semiconductor products. Accordingly, abnormal process errors of the semiconductor processing equipments become major obstacles to obtain a good quality of semiconductor product as well as cause economic loss and time loss.

One of the semiconductor processing equipments is a plasma reactor. The main use of the plasma reactor is to etch a wafer surface according to a specific pattern or deposit deposition materials on a wafer top surface according to a specific pattern. The plasma reactor includes a plasma reaction chamber and a plasma reaction controller. During an etch or deposition process, a target wafer is mounted within the plasma reaction chamber and plasma reaction conditions such as a pressure, a reaction gas, and power within the plasma reaction chamber are controlled by the plasma reaction controller. For the plasma reaction controller to accurately control the plasma reaction conditions is of much importance, for example, to prevention of process errors such as over-etch during a plasma etch process. The plasma reaction controller has to accurately detect an in-chamber status in order for the plasma reaction controller to accurately control the plasma reaction conditions within the plasma reaction chamber. For this, a conventional plasma reactor for detecting an etch endpoint using a monochromator has been developed.

The conventional plasma reactor includes a reaction chamber, an optical fiber cable, the monochromator, and an endpoint detection device.

The optical fiber cable collects a single wavelength light emitted from the inside of the reaction chamber through a window provided in an outer sidewall of the reaction chamber and forwards the collected lights to the monochromator. The single wavelength light can be lights generated when a component (e.g., etched material) serving as a criterion for determining an etch endpoint of a target wafer reacts with plasma.

The monochromator converts the single wavelength light received from the optical fiber cable into a voltage level signal and outputs the voltage level signal to the endpoint detection device.

The endpoint detection device detects an etch endpoint on the basis of the voltage level signal received from the monochromator. For example, the progress of an etch process brings about a reduction of etched material and resultantly, a reduction of even lights generated by the etched material. In conclusion, the endpoint detection device determines that an etch endpoint is a time point of reduction of light generated by the etched material, using the voltage level signal received from the monochromator.

As described above, the conventional plasma reactor detects an etch endpoint using the single wavelength light. However, a wavelength of lights generated by etched materials is distributed over several frequency bands and therefore, it is very difficult to select one wavelength of most significance serving as a criterion for determining an etch endpoint. Also, as a percentage of total area to open area of a target wafer is extremely less, a noise of the single wavelength light increases. This is shown in detail in FIGS. 1A to 1C.

FIG. 1A shows a time-dependent variation of a prediction value for determining an etch endpoint when an open area rate is equal to 3%. Like FIG. 1A, FIGS. 1B and 1C each show time-dependent variations of prediction values for determining etch endpoints when open area rates are equal to 0.7% and 0.5%. In FIG. 1A, a waveform shows a clear etch endpoint (E) because of a large difference between prediction values before and after the etch endpoint (E). However, in FIGS. 1B and 1C, a waveform shows an unclear etch endpoint (E) because of a very small difference between prediction values before and after the etch endpoint (E). As described above, in a method for detecting an etch endpoint using a single wavelength, when the percentage of total area to open area is a few percents or less, the etch endpoint is not actually detected with accuracy.

For a solution to disadvantages of the etch endpoint detection method using the single wavelength, a research on a method for detecting an endpoint using a whole wavelength has been conducted a lot. To realize this, Principal Component Analysis (PCA), a kind of multivariate statistic analysis method, has been used. PCA (Jackson, 1981) is a method of representing a number of variate values by one or a few synthetic indicators (main components) with no information loss as possible. PCA includes converting lights of several wavelengths, which are emitted from the inside of a chamber with execution of an etch process, into voltage level data, normalizing the voltage level data, processing the normalized data by PCA, computing part of result values obtained by PCA processing and the normalized data, and detecting an etch endpoint on the basis of the result values of the computing. However, in a conventional endpoint detection method using PCA, a detection speed is very slow because it actually takes a long time to real-time normalize voltage level signals (that is, Optical Emission Spectrometer (OES) data). In conclusion, PCA is almost impossible to real-time determine an in-chamber status quickly and thereby the plasma reaction controller is impossible to real-time control reaction conditions within a plasma reaction chamber as well. This problem becomes more serious because of the recent development of sensors to have as better operation performance as the sensors receive light signals of thousands of wavelengths at several times even for one second. That is, the sensors can receive a large amount of light signals with the improvement of operation performance of the sensors; however, it takes a very long time to store and normalize voltage level data corresponding to the large amount of received light signals. Accordingly, an endpoint detection speed gets slower and resultantly, it is impossible to control plasma reaction conditions in real time.

SUMMARY OF THE INVENTION

An aspect of exemplary embodiments of the present invention is to address at least the problems and/or disadvantages and to provide at least the advantages described below. Accordingly, an aspect of exemplary embodiments of the present invention is to provide an endpoint detection device for, with execution of a real-time process wafer etch or deposition process, computing OES data generated in real time and loading vectors previously calculated in a previous etch or deposition process, and generating a product value for determining an etch or deposition endpoint, thereby detecting an endpoint without real-time normalization of the OES data, increasing a detection speed, and realizing a real-time control of a plasma reactor.

Another aspect of exemplary embodiments of the present invention is to provide a plasma reactor comprising the endpoint detection device for, with execution of a real-time process wafer etch or deposition process, computing OES data generated in real time and loading vectors previously calculated during a previous etch or deposition process, and generating a product value for determining an etch or deposition endpoint, thereby detecting an endpoint without real-time normalization of the OES data, increasing a detection speed, and realizing a real-time control of a plasma reactor.

A further another aspect of exemplary embodiments of the present invention is to provide an endpoint detection method for, with execution of a real-time process wafer etch or deposition process, computing OES data generated in real time and loading vectors previously calculated during a previous etch or deposition process, and generating a product value for determining an etch or deposition endpoint, thereby detecting an endpoint without real-time normalization of the OES data, increasing a detection speed, and realizing a real-time control of a plasma reactor.

According to one aspect of exemplary embodiments of the present invention, there is provided an endpoint detection device. The device includes an Optical Emission Spectrometer (OES) data operation unit, a data selector, a product generator, a Support Vector Machine (SVM), and an endpoint determiner. The OES data operation unit processes reference OES data by normalization and Principal Component Analysis (PCA), outputs linear reference loading vectors and rate values of reference principal components, and outputs reference ranking values on the basis of the linear reference loading vectors. The data selector first selects part of the linear reference loading vectors on the basis of the rate values of the reference principal components, selects part of the reference OES data or selects part of process OES data on the basis of the reference ranking values, and second selects part of the first selected linear reference loading vectors on the basis of the reference ranking values. The product generator outputs at least one reference product value on the basis of the first selected linear reference loading vectors and the reference OES data. The SVM performs regression on the basis of the selected reference OES data and the at least one reference product value, generates nonlinear reference loading vectors, and periodically outputs a prediction product value on the basis of the second selected linear reference loading vectors, the nonlinear reference loading vectors, and the selected process OES data. The endpoint determiner detects a process wafer etch or deposition endpoint on the basis of the periodically received prediction product value and outputs a detection signal.

First lights of a whole wavelength emitted from the inside of a plasma reaction chamber are converted into the reference OES data by a spectrometer during a reference wafer etch or deposition process. Second lights of a whole wavelength emitted from the inside of the plasma reaction chamber are converted into the process OES data by the spectrometer during a process wafer etch or deposition process executed after the reference wafer etch or deposition process. The reference ranking values represent a ranking for the intensity of the first lights of the whole wavelength. The linear reference loading vectors each correspond to one-dimensional function values expressed by the reference OES data and the nonlinear reference loading vectors each correspond to S-dimensional (S: integer larger than 1) function values expressed by the selected process OES data.

According to another aspect of exemplary embodiments of the present invention, there is provided an endpoint detection device. The device includes a data selector, an OES data operation unit, a product generator, and an endpoint determiner. The data selector sets a data selection range and outputting an operation control signal in response to a data selection signal, selects part of reference OES data on the basis of the data selection range during a reference wafer etch or deposition process, and selects part of process OES data on the basis of the data selection range during a process wafer etch or deposition process. The OES data operation unit processes the selected reference OES data by normalization and PCA and outputs linear reference loading vectors in response to the operation control signal. The product generator periodically outputs a prediction product value on the basis of the linear reference loading vectors and the selected process OES data. The endpoint determiner detects a process wafer etch or deposition endpoint and outputs a detection signal on the basis of the periodically received prediction product value.

First lights of a whole wavelength emitted from the inside of a plasma reaction chamber are converted into the reference OES data by a spectrometer during a reference wafer etch or deposition process. Second lights of a whole wavelength emitted from the inside of the plasma reaction chamber are converted into the process OES data by the spectrometer during a process wafer etch or deposition process executed after the reference wafer etch or deposition process. The linear reference loading vectors each correspond to one-dimensional function values expressed by the reference OES data.

According to a further another aspect of exemplary embodiments of the present invention, there is provided a plasma reactor including a plasma reaction chamber, a spectrometer, an optical fiber cable, an endpoint detection device, and a plasma reaction controller. A reference wafer or a process wafer is mounted within the plasma reaction chamber. The spectrometer converts first lights of a whole wavelength emitted from the inside of the plasma reaction chamber into reference OES data during a reference wafer etch or deposition process or converts second lights of a whole wavelength emitted from the inside of the plasma reaction chamber into process OES data during a process wafer etch or deposition process executed after the reference wafer etch or deposition process. The optical fiber cable collects the first or second lights of the whole wavelength emitted from the inside of the plasma reaction chamber through a window provided at an outer wall of the plasma reaction chamber and forwards the collected lights to the spectrometer during the reference wafer or process wafer etch or deposition process. The endpoint detection device detects a process wafer etch or deposition endpoint and outputs a detection signal on the basis of the reference OES data and the process OES data. The plasma reaction controller controls an etch or deposition condition within the plasma reaction chamber in response to the detection signal.

The endpoint detection device includes an OES data operation unit, a data selector, a product generator, an SVM, and an endpoint determiner. The OES data operation unit processes the reference OES data by normalization and PCA, outputs linear reference loading vectors and rate values of reference principal components, and outputs reference ranking values on the basis of the linear reference loading vectors. The data selector first selects part of the linear reference loading vectors on the basis of the rate values of the reference principal components, selects part of the reference OES data or selecting part of the process OES data on the basis of the reference ranking values, and second selects part of the first selected linear reference loading vectors on the basis of the reference ranking values. The product generator outputs at least one reference product value on the basis of the first selected linear reference loading vectors and the reference OES data. The SVM performs regression on the basis of the selected reference OES data and the at least one reference product value, generates nonlinear reference loading vectors, and periodically outputs a prediction product value on the basis of the second selected linear reference loading vectors, the nonlinear reference loading vectors, and the selected process OES data. The endpoint determiner detects a process wafer etch or deposition endpoint on the basis of the periodically received prediction product value and outputting a detection signal.

The reference ranking values represent a ranking for the intensity of the first lights of the whole wavelength. The linear reference loading vectors each correspond to one-dimensional function values expressed by the reference OES data and the nonlinear reference loading vectors each correspond to S-dimensional (S: integer larger than 1) function values expressed by the selected process OES data.

According to a yet another aspect of exemplary embodiments of the present invention, there is provided a plasma reactor including a plasma reaction chamber, a spectrometer, an optical fiber cable, an endpoint detection device, and a plasma reaction controller. A reference wafer or a process wafer is mounted within the plasma reaction chamber. The spectrometer converts first lights of a whole wavelength emitted from the inside of the plasma reaction chamber into reference OES data during a reference wafer etch or deposition process or converts second lights of a whole wavelength emitted from the inside of the plasma reaction chamber into process OES data during a process wafer etch or deposition process executed after the reference wafer etch or deposition process. The optical fiber cable collects the first or second lights of the whole wavelength emitted from the inside of the plasma reaction chamber through a window provided at an outer wall of the plasma reaction chamber and forwards the collected lights to the spectrometer during the reference wafer or process wafer etch or deposition process. The endpoint detection device detects a process wafer etch or deposition endpoint and outputs a detection signal on the basis of the reference OES data and the process OES data. The plasma reaction controller controls an etch or deposition condition within the plasma reaction chamber in response to the detection signal.

The endpoint detection device includes a data selector, an OES data operation unit, a product generator, and an endpoint determiner. The data selector sets a data selection range and outputs an operation control signal in response to a data selection signal, selects part of reference OES data on the basis of the data selection range during the reference wafer etch or deposition process, and selects part of process OES data on the basis of the data selection range during the process wafer etch or deposition process. The OES data operation unit processes the selected reference OES data by normalization and PCA and outputs linear reference loading vectors in response to the operation control signal. The product generator periodically outputs a prediction product value on the basis of the linear reference loading vectors and the selected process OES data. The endpoint determiner detects a process wafer etch or deposition endpoint and outputs a detection signal on the basis of the periodically received prediction product value. The linear reference loading vectors each correspond to one-dimensional function values expressed by the reference OES data.

According to a still another aspect of exemplary embodiments of the present invention, there is provided an endpoint detection method including processing, by an OES data operation unit, reference OES data by normalization and PCA and generating linear reference loading vectors, rate values of reference principal components, and reference ranking values; making an SVM learn on the basis of the linear reference loading vectors, the rate values of the reference principal components, the reference ranking values, and the reference OES data; selecting, by a data selector, part of the process OES data on the basis of the reference ranking values; periodically generating a prediction product value using the learning SVM and the selected process OES data; and detecting, by an endpoint determiner, a process wafer etch or deposition endpoint on the basis of the prediction product value and outputting a detection signal.

The reference OES data are data obtained by converting, by a spectrometer, first lights of a whole wavelength emitted from the inside of a plasma reaction chamber during a reference wafer etch or deposition process. The process OES data are data obtained by converting, by the spectrometer, second lights of a whole wavelength emitted from the inside of the plasma reaction chamber during a process wafer etch or deposition process executed after the reference wafer etch or deposition process. The linear reference loading vectors each correspond to one-dimensional function values expressed by the reference OES data. The reference ranking values represent a ranking for the intensity of the first lights of the whole wavelength.

According to a still another aspect of exemplary embodiments of the present invention, there is provided an endpoint detection method including displaying, by a display unit, reference OES data into which first lights of a whole wavelength emitted from the inside of a plasma reaction chamber are converted by a spectrometer during a reference wafer etch or deposition process, in a three-dimensional graphic picture; setting a data selection range of a data selector depending on the display result; selecting, by the data selector, part of the reference OES data on the basis of the data selection range; normalizing and PCA processing, by an OES data operation unit, the selected reference OES data and generating linear reference loading vectors; selecting, by the data selector, part of process OES data on the basis of the data selection range; periodically generating, by a product generator, a prediction product value on the basis of the linear reference loading vectors and the selected process OES data; and detecting, by an endpoint determiner, a process wafer etch or deposition endpoint and outputting a detection signal on the basis of the prediction product value.

The process OES data are data obtained by converting, by the spectrometer, second lights of a whole wavelength emitted from the inside of the plasma reaction chamber during a process wafer etch or deposition process executed after the reference wafer etch or deposition process. The linear reference loading vectors each correspond to one-dimensional function values expressed by the reference OES data.

BRIEF DESCRIPTION OF THE DRAWINGS

The above and other objects, features and advantages of the present invention will become more apparent from the following detailed description when taken in conjunction with the accompanying drawings in which:

FIGS. 1A to 1C are graphs illustrating a time-dependent variation of an endpoint prediction value generated by a conventional endpoint detection method;

FIG. 3 is a table illustrating an example of reference OES data of FIG. 2;

FIG. 4 is a diagram illustrating a computing process of an OES data operation unit of FIG. 2;

Throughout the drawings, the same drawing reference numerals will be understood to refer to the same elements, features and structures.

DETAILED DESCRIPTION OF THE INVENTION

Exemplary embodiments of the present invention will now be described in detail with reference to the annexed drawings. In the following description, a detailed description of known functions and configurations incorporated herein has been omitted for conciseness.

Figure 2:
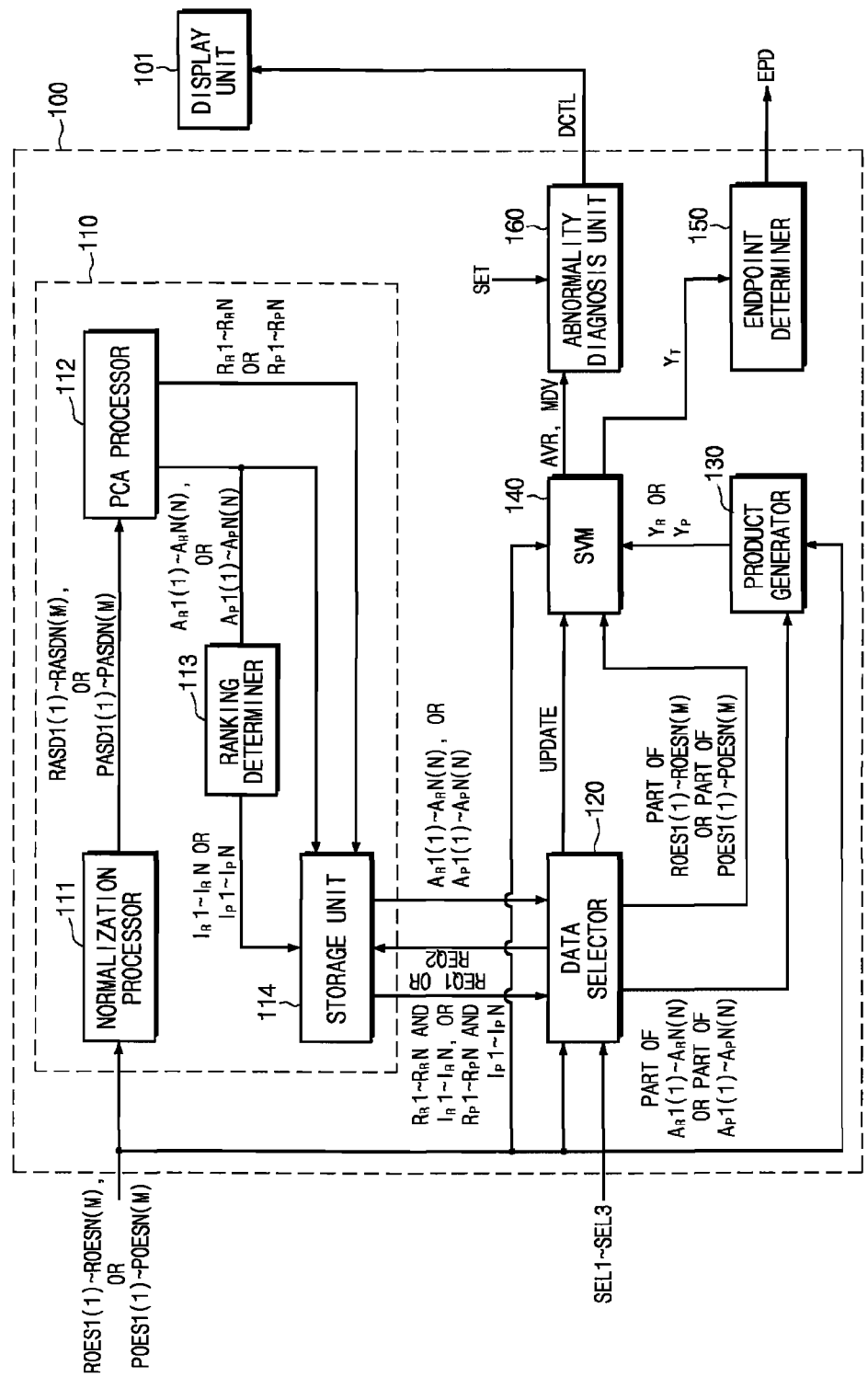
FIG. 2 is a block diagram illustrating an endpoint detection device according to an exemplary embodiment of the present invention.

FIG. 2 is a block diagram illustrating an endpoint detection device according to an exemplary embodiment of the present invention.

Referring to FIG. 2, the endpoint detection device 100 includes an OES data operation unit 110, a data selector 120, a product generator 130, an SVM 140, an endpoint determiner 150, and an abnormality diagnosis unit 160. The OES data operation unit 110 includes a normalization processor 111, a PCA processor 112, a ranking determiner 113, and a storage unit 114.

During a reference wafer etch or deposition process, the normalization processor 111 normalizes reference OES data (ROES1(1) to ROESN(M)) (N, M: integers) and outputs reference average scaling data (RASD1(1) to RASDN(M)). Here, "N" is equal to the number of wavelengths sampled at each sampling time and "M" is equal to the number of samples for each wavelength. The reference OES data (ROES1(1) to ROESN(M)) are data obtained by converting, by a spectrometer 330 (FIG. 14), whole wavelength lights (hereinafter, referred to as "first lights") emitted from the inside of a plasma reaction chamber 310 (FIG. 14) when a reference wafer is etched or deposited. The reference OES data (ROES1(1) to ROESN(M)) can be expressed in an M×N matrix. Also, the reference average scaling data (RASD1(1) to RASDN(M)) can be expressed in an M×N matrix.

After the reference wafer etch or deposition process, during a process wafer etch or deposition process, the normalization processor 111 normalizes process OES data (POES1(1) to POESN(M)) and outputs process average scaling data (PASD1(1) to PASDN(M)). The process OES data (POES1(1) to POESN(M)) are data obtained by converting, by the spectrometer 330, whole wavelength lights (hereinafter, referred to as "second lights") emitted from the inside of the plasma reaction chamber 310 when a process wafer is etched or deposited. Like the reference OES data (ROES1(1) to ROESN(M)), the process OES data (POES1(1) to POESN(M)) can be expressed in an M×N matrix as well. The process average scaling data (PASD1(1) to PASDN(M)) can be also expressed in an M×N matrix. Values of the reference OES data (ROES1(1) to ROESN(M)) or the process OES data (POES1(1) to POESN(M)) output from the spectrometer 330 are varied dependent on time as shown in FIG. 3.

During the reference wafer etch or deposition process, the PCA processor 112 processes, by PCA, the reference average scaling data (RASD1(1) to RASDN(M)) and outputs rate values ($R_R1$ to $R_RN$) of reference principal components (PC1 to PCN) (N: integer representing the number of wavelengths) and linear reference loading vectors ($A_R1(1)$ to $A_R1(N)$, $A_R2(1)$ to $A_R2(N)$, ..., $A_RN(1)$ to $A_RN(N)$). The linear reference loading vectors ($A_R1(1)$ to $A_R1(N)$) are loading vectors for the reference main component (PC1). The linear reference loading vectors ($A_R2(1)$ to $A_R2(N)$) are loading vectors for the reference main component (PC2). That is, the linear reference loading vectors exist by "N" counts for each reference main component. The rate values ($R_R1$ to $R_RN$) of the reference principal components (PC1 to PCN) represent a significance degree at each wavelength.

The PCA processing of the PCA processor 112 is described below in more detail with reference to FIGS. 4 and 5. In general, PCA is a method for processing, by eigenvector decomposition, a covariance matrix of a process variable matrix. For example, the "n" number of data (that is, $X_{11}$, $X_{22}$, ..., $X_{pn}$) whose variate is denoted by "p" each can be expressed using the "n" number of points in p-dimensional space. However, when p>3, it is difficult to define a position relationship between the respective points. In this case, PCA can be called a method for representing in low dimension while keeping the position relationship between the "n" number of points as possible. Thus, together with a Partial Least Squares (PLS) method, PCA is widely used because many existing variables are easily treated in a semiconductor manufacturing process.

In mathematics, PCA is a method for decomposing a covariance matrix of a process variable matrix into eigenvectors. For instance, assuming a data matrix (X) (m×n) with the "m" number of samples and the "n" number of variables, a covariance matrix equation of the data matrix (X) (m×n) can be expressed in Equation 1:

$$\text{cov}(X) = \frac{X^T X}{m-1} \quad (1)$$

where, cov(X): covariance matrix, and $X^T$: transposition matrix of X.

The PCA processor 112 calculates the covariance matrix (cov(X)) by applying the data matrix (X) comprised of the reference average scaling data (RASD1(1) to RASDN(M)) to Equation 1. After that, the PCA processor 112 calculates an eigenvalue (λe) and an eigenvector (Ve) using the covariance matrix (cov(X)). This is described in more detail with reference to FIG. 4. A data matrix (X') comprised of the reference average scaling data (RASD1(1) to RASDN(M)) is a normalization of the data matrix (X) comprised of the reference OES data (60, 58, 25, . . . , 45) at each wavelength (x1, x2, and x3) sampled every sampling time (t1 to t7), for example. In FIG. 4, for simplicity, an example of only reference OES data at each sampling time corresponding to three wavelengths is shown using specific numerical values. The PCA processor 112 calculates the covariance matrix (cov(X)) from the data matrix (X'), using Equation 1. After that, the PCA processor 112 calculates a data matrix (D) defined in Equation 2:

$$D = cov(X) * cov(X)^T \qquad (2)$$

where, $cov(X)^T$: a transposition matrix of cov(x).

Next, the PCA processor 112 calculates an eigenvalue matrix ($\lambda$e) and an eigenvector matrix (Ve) by solving an eigenvector problem about the data matrix (D). The PCA processor 112 calculates a principal component matrix (P) using the eigenvalue matrix ($\lambda$e). Desirably, the principal component matrix (P) can be calculated by computing a square root of the eigenvalue matrix ($\lambda$e). Among elements constituting the principal component matrix (P), diagonally arrayed elements correspond to the reference principal components (PC1 to PC3). FIG. 4 shows, for instance, only the reference principal components (PC1 to PC3) for three wavelengths (that is, three pieces of reference OES data). In actual, however, even the reference principal components are generated in proportional to the number of reference OES data because a large number of wavelengths are sampled at each sampling time zone by the spectrometer 330 as only part of them is shown in FIG. 3. In the eigenvector matrix (Ve), "A1" denotes values of the linear reference loading vectors ($A_R1(1)$ to $A_R1(3)$) for the reference principal component (PC1), "A2" denotes values of the linear reference loading vectors ($A_R2(1)$ to $A_R2(3)$) for the reference principal component (PC2), and "A3" denotes values of the linear reference loading vectors ($A_R3(1)$ to $A_R3(3)$) for the reference principal component (PC3).

The PCA processor 112 calculates ratio values for each principal component using the reference principal components (PC1 to PC3). The ratio value ($R_RJ$) at each reference principal component can be expressed in Equation 3:

$$R_RJ = \frac{PCJ}{\sum_{i=1}^{N} PCi} \times 100 \qquad (3)$$

where,

N: integer representing total number of reference principal components, and

J: integer satisfying condition of 0<J≦N.

During the process wafer etch or deposition process, the PCA processor 112 PCA processes process average scaling data (PASD1(1) to PASDN(M)) and outputs linear process loading vectors ($A_P1(1)$ to $A_P1(N)$, $A_P2(1)$ to $A_P2(N)$, . . . , $A_PN(1)$ to $A_PN(N)$) and rate values ($R_P1$ to $R_PN$) of process principal components (PC1 to PCN) (N: integer). A process of PCA processing the process average scaling data (PASD1(1) to PASDN(M)) in the PCA processor 112 is similar with the process of PCA processing the reference average scaling data (RASD1(1) to RASDN(M)) and thus, its description is omitted.

Referring again to FIG. 2, the ranking determiner 113 outputs reference ranking values ($\lambda_R1$ to $\lambda_RN$) (N: integer representing the total number of wavelengths) on the basis of the linear reference loading vectors ($A_R1(1)$ to $A_R1(N)$, $A_R2(1)$ to $A_R2(N)$, . . . , $A_RN(1)$ to $A_RN(N)$) during the reference wafer etch or deposition process. The reference ranking values ($\lambda_R1$ to $\lambda_RN$) denote a ranking for the intensity of the first lights. Each reference ranking value ($\lambda_RQ$) can be expressed in Equation 4:

$$\lambda_R Q = \sqrt{\sum_{i=1}^{N} (A_R i(Q))^2} \qquad (4)$$

where,

Q: integer satisfying condition of 0<Q≦N.

Also, the ranking determiner 113 outputs process ranking values ($\lambda_P1$ to $\lambda_PN$) (N: integer representing the total number of wavelengths) on the basis of the linear process loading vectors ($A_P1(1)$ to $A_P1(N)$, $A_P2(1)$ to $A_P2(N)$, . . . , $A_PN(1)$ to $A_PN(N)$) during the process wafer etch or deposition process. Each of the reference ranking values ($\lambda_P1$ to $\lambda_PN$) denote a ranking for the intensity of the second lights. A process of calculating each process ranking value ($\lambda_PQ$) (0<Q≦N) in the ranking determiner 113 is similar with the process described in Equation 4 and thus, its detailed description is omitted.

During the reference wafer etch or deposition process, the storage unit 114 stores the linear reference loading vectors ($A_R1(1)$ to $A_R1(N)$, $A_R2(1)$ to $A_R2(N)$, . . . , $A_RN(1)$ to $A_RN(N)$) and the rate values ($R_R1$ to $R_RN$) of the reference principal components (PC1 to PCN) received from the PCA processor 112, and stores the reference ranking values ($\lambda_R1$ to $\lambda_RN$) received from the ranking determiner 113.

Also, during the process wafer etch or deposition process, the storage unit 114 stores the linear process loading vectors ($A_P1(1)$ to $A_P1(N)$, $A_P2(1)$ to $A_P2(N)$, . . . , $A_PN(L)$ to $A_PN(N)$) and the rate values ($R_P1$ to $R_PN$) of the process principal components (PC1 to PCN) received from the PCA processor 112, and stores the process ranking values ($\lambda_P1$ to $\lambda_PN$) received from the ranking determiner 113. Here, the storage unit 114 can consecutively store linear process loading vectors, rate values of process principal components, and process ranking values generated whenever the process wafer etch or deposition process is executed. Alternatively, after erasing linear process loading vectors, rate values of process principal components, and process ranking values generated during a previous process wafer etch or deposition process, the storage unit 114 can also store linear process loading vectors, rate values of the process principal components, and process ranking values generated when a new process wafer etch or deposition process is executed. The storage unit 114 provides storage values to the data selector 120 in response to request signals (REQ1 to REQ2) from the data selector 120.

The data selector 120 selects part of the linear reference loading vectors ($A_R1(1)$ to $A_R1(N)$, $A_R2(1)$ to $A_R2(N)$, . . . , $A_RN(1)$ to $A_RN(N)$) on the basis of the rate values ($R_R1$ to $R_RN$) of the reference principal components. In more detail, the data selector 120 selects only the linear reference loading vectors of the reference principal components corresponding to a preset rate value among the rate values ($R_R1$ to $R_RN$) of the reference principal components. For example, it is assumed that a rate value preset to the data selector 120 is equal or more than 80%, the rate value ($R_R1$) of the reference principal component (PC1) is equal to 70%, and the rate value ($R_R2$) of the reference principal component (PC2) is equal to 15%. In this case, the data selector 120 selects only the linear reference loading vectors ($A_R1(1)$ to $A_R1(N)$ and $A_R2(1)$ to $A_R2(N)$) of the reference principal components (PC1 and PC2) because a sum of the rate values ($R_R1$ and $R_R2$) is equal to 85%. Here, a user can preset the rate value to the data selector 120 through an input unit 360 (FIG. 14) that includes a plurality of keys. That is, if the user inputs a rate value to be preset through the input unit 360, the input unit 360 outputs a selection signal (SEL1) and the data selector 120 sets the rate value in response to the selection signal (SEL1). Likely, the data selector 120 selects part of the linear process loading vectors ($A_P1(1)$ to $A_P1(N), A_P2(1)$ to $A_P2(N), \ldots, A_PN(1)$ to $A_PN(N)$) on the basis of the rate values ($R_P1$ to $R_PN$) of the process principal components.

Figure 14:
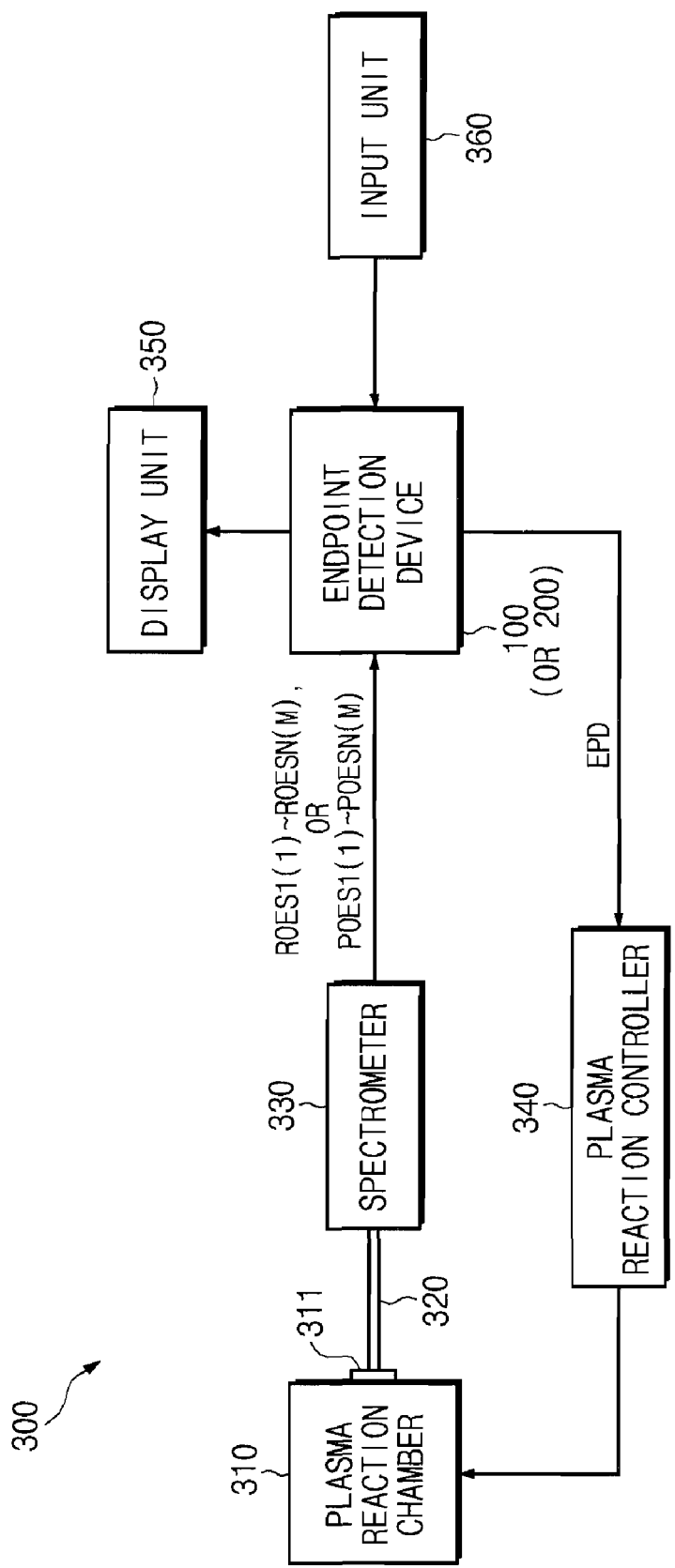
FIG. 14 is a block diagram schematically illustrating a plasma reactor including an endpoint detection device according to the present invention.

The data selector 120 selects part of the reference OES data (ROES1(1) to ROESN(M)) or selects part of the process OES data (POES1(1) to POESN(M)) on the basis of the reference ranking values ($\lambda_R1$ to $\lambda_RN$). Also, on the basis of the reference ranking values ($\lambda_R1$ to $\lambda_RN$), the data selector 120 additionally selects part of the linear reference loading vectors (e.g., $A_R1(1)$ to $A_R1(N)$ and $A_R2(1)$ to $A_R2(N)$) that have been selected on the basis of the rate values ($R_R1$ to $R_RN$). In more detail, the data selector 120 selects only reference OES data or process OES data and linear reference loading vectors each corresponding to a wavelength(s) of a preset ranking value(s). For instance, it is assumed that the linear reference loading vectors selected by the data selector 120 on the basis of the rate values ($R_R1$ to $R_RN$) are equal to $A_R1(1)$ to $A_R1(N)$ and $A_R2(1)$ to $A_R2(N)$, the ranking value preset to the data selector 120 is equal to a high rank 10%, and the ranking values corresponding to the high rank 10% are equal to $\lambda_R1$ and $\lambda_R2$. In this case, the data selector 120 selects reference OES data (ROES1(1) to ROES1(M) and ROES2(1) to ROES2(M)) or process OES data (POES1(1) to POES1(M) and POES2(1) to POES2(M)) corresponding to wavelengths (x1 and x2) and selects linear reference loading vectors ($A_R1(1), A_R1(2), A_R2(1)$, and $A_R2(2)$) corresponding to the wavelengths (x1 and x2) because the ranking values corresponding to the high rank 10% are equal to $\lambda_R1$ and $\lambda_R2$. Here, the user can preset the ranking value to the data selector 120 through the input unit 360 (FIG. 14). That is, if the user selects a ranking value to be preset through the input unit 360, the input unit 360 outputs a selection signal (SEL2) and the data selector 120 sets the ranking value in response to the selection signal (SEL2). The ranking value set to the data selector 120 does not necessarily need to be a high rank value and can be also be a percent value of a middle rank, low rank, or desired rank zone.

Likely, on the basis of the process ranking values ($\lambda_P1$ to $\lambda_PN$), the data selector 120 additionally selects part of the linear process loading vectors (part of $A_P1(1)$ to $A_P1(N), A_P2(1)$ to $A_P2(N), \ldots, A_PN(1)$ to $A_PN(N)$) that have been selected on the basis of the rate values ($R_P1$ to $R_PN$). Likely, the data selector 120 selects part of the process OES data (POES1(1) to POESN(M)) on the basis of the process ranking values ($\lambda_P1$ to $\lambda_PN$). The data selector 120 outputs an update request signal (UPDATE) to the SVM 140 when the number of times of execution of the process wafer etch or deposition process reaches the set number of times. The data selector 120 can output the update request signal (UPDATE) to the SVM 140 even during the reference wafer etch or deposition process. The user can set the number of times of process execution to the data selector 120 through the input unit 360. In detail, if the user inputs the number of times of process execution through the input unit 360, the input unit 360 outputs a selection signal (SEL3) and the data selector 120 sets the number of times of process execution in response to the selection signal (SEL3).

On the basis of the linear reference loading vectors (part of $A_R1(1)$ to $A_R1(N), A_R2(1)$ to $A_R2(N), \ldots, A_RN(1)$ to $A_RN(N)$) that are selected by the data selector 120 on the basis of the rate values ($R_R1$ to $R_RN$) and the reference OES data (ROES1(1) to ROESN(M)), the product generator 130 outputs at least one reference product value ($Y_R$). When "X" denotes an M×N data matrix comprised of the reference OES data (ROES1(1) to ROESN(M)) and "A" denotes a data matrix comprised of the linear reference loading vectors (part of $A_R1(1)$ to $A_R1(N), A_R2(1)$ to $A_R2(N), \ldots, A_RN(1)$ to $A_RN(N)$) selected on the basis of the rate values ($R_R1$ to $R_RN$), a reference product value ($Y_R(U)$) corresponding to a U-th reference principal component (PCU) can be expressed in Equation 5:

$$Y_R(U) = X * A(U) \quad (5)$$

where,

A(U): linear reference loading vectors ($A_RU(1)$ to $A_RU(N)$) of reference principal component (PCU).

For example, when the linear reference loading vectors selected by the data selector 120 on the basis of the rate values ($R_R1$ to $R_RN$) are equal to $A_R1(1)$ to $A_R1(N)$ and $A_R2(1)$ to $A_R2(N)$, Equation 5 can be expressed in more detail in Equation 6:

$$Y_R(1) = A_R1(1) \cdot X1 + A_R1(2) \cdot X2 + \ldots + A_R1(N) \cdot X_N,$$

$$Y_R(2) = A_R2(1) \cdot X1 + A_R2(2) \cdot X2 + \ldots + A_R2(N) \cdot X_N \quad (6)$$

where,

X1 to XN: one-dimensional functions representing reference OES data corresponding to whole wavelength sampled at same sampling time among reference OES data (ROES1(1) to ROESN(M)).

The reference OES data corresponding to the whole wavelength at each sampling time are shown in Table 1 below in more detail.

TABLE 1

| Sampling time | Reference OES data |
|---|---|
| T1 | ROES1(1) to ROESN(1) |
| T2 | ROES1(2) to ROESN(2) |
| T3 | ROES1(3) to ROESN(3) |
| . | . |
| . | . |
| TM | ROES1(M) to ROESN(M) |

In Table 1, the "M" number of data (that is, reference OES data) is sampled for each wavelength at a set time interval. Consequently, the product generator 130 periodically outputs the reference product value ($Y_R(U)$) on the basis of the reference OES data sampled once every sampling time.

Figure 6:
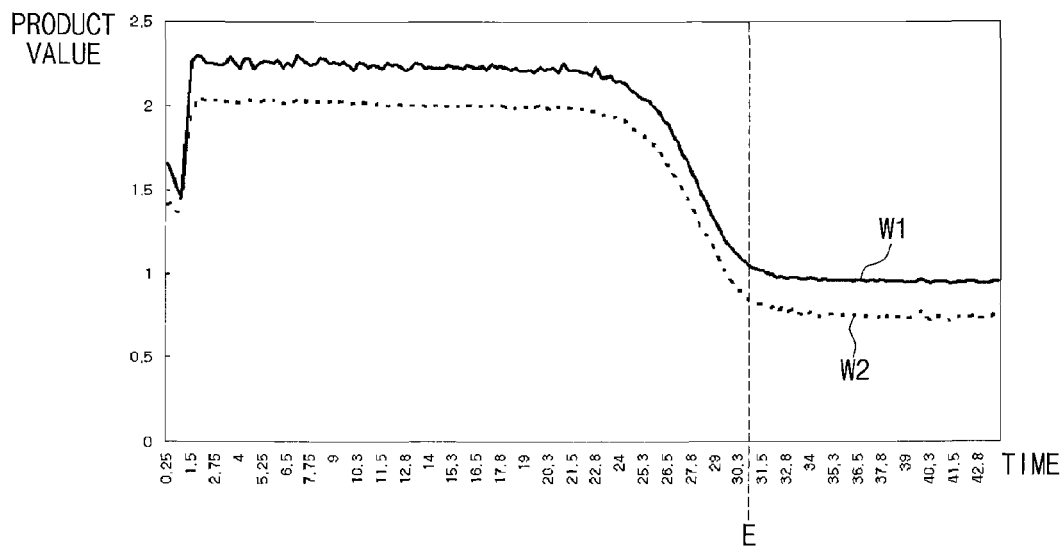
FIG. 6 is a graph showing waveforms each formed by actual product values and prediction product values of FIG. 2.

The product generator 130 outputs an actual product value ($Y_P$) on the basis of the linear process loading vectors (part of $A_P1(1)$ to $A_P1(N), A_P2(1)$ to $A_P2(N), \ldots, A_PN(1)$ to $A_PN(N)$) that are selected by the data selector 120 on the basis of the rate values ($R_P1$ to $R_PN$) and the process OES data (POES1(1) to POESN(M). A process of calculating the actual product value ($Y_P$) in the product generator 130 is similar with the process described with reference to Equations 5 and 6 and its detailed description is omitted. Like the operation of outputting the reference product value ($Y_R(U)$), the product generator 130 periodically outputs the actual product value ($Y_P$) on the basis of the process OES data sampled once every sampling time. The actual product values ($Y_P$) periodically output from the product generator 130 with the lapse of time form one waveform (W2) as shown in FIG. 6.

The SVM 140 executes a learning operation through regression in response to an update request signal (UPDATE). In detail, the SVM 140 performs regression and generates nonlinear reference loading vectors ($A_{NR}1$ to $A_{NR}G$) (G: integer) on the basis of the reference OES data (part of ROES1(1) to ROESN(M)) that are selected on the basis of the rate values ($R_R 1$ to $R_R N$) and the reference product value ($Y_R(U)$). As a result, the SVM 140 learns the linear reference loading vectors ($A_R 1(1)$ to $A_R 1(N), A_R 2(1)$ to $A_R 2(N), \ldots, A_R N(1)$ to $A_R N(N)$) and the nonlinear reference loading vectors ($A_{NR} 1$ to $A_{NR} G$) through regression. Also, the SVM 140 can learn by one reference product value (that is, a reference product value (e.g., $Y_R(1)$) corresponding to one principal component) or can learn by a rate of a plurality of reference product values (that is, reference product values (e.g. $Y_R(1)$ and $Y_R(2)$) corresponding to a plurality of principal components).

Though the reference product value ($Y_R$) is calculated on the basis of Equation 6 including only the one-dimensional functions, the reference product value ($Y_R$) is a value calculated on the basis of the reference OES data (ROES1(1) to ROESN(M)) corresponding to not a partial selected wavelength but a whole wavelength. Accordingly, the reference product value ($Y_R$) actually approximates a product value (referring to Equation 23 below) calculated using the OES data corresponding to the partial selected wavelength and the linear and nonlinear loading vectors.

A general operation principle of the SVM 140 and a nonlinear regression equation associated with regression are described below.

SVM, a solution to a pattern recognition problem, is widely used as a learning algorithm for solving a binary classification problem. For example, when given learning data (S) defined as $(x_1, y_1), \ldots, (x_n, y_n), x_i \in R^n, y_i \in \{+1, -1\}$, SVM finds an optimal hyperplane accurately classifying the learning data (S) into two classes. Here, "$x_i$" denotes i-th data expressed with an n-dimensional vector and "$y_i$" denotes a label expressing a class (+1 or −1) of i-th data. SVM finds an optimal hyperplane classifying the learning data into two classes while maximizing a minimum distance between each class and a hyperplane. This can be expressed in Equation 7 below:

$$y_i(w \cdot x_i + b) \geq 1, (i=1, 2, \ldots, n, n: \text{integer}) \quad (7)$$

where, $w \in R^n$, $b \in R^n$, and

R: real number space.

"w", "b" are defined as hyperplanes of Equation 8 below. These are defined as separating hyperplanes.

$$w \cdot x_i + b = 0 \quad (8)$$

When a normal distance of "w" is expressed as $\|w\|$, a distance ($d_i$) from the separating hyperplane (w, b) to the vector ($x_i$) can be expressed in Equation 9 below:

$$d_i = \frac{w \cdot x_i + b}{\|w\|} \quad (9)$$

If Equation 7 is transformed, "$y_i$" can be expressed in Equation 10 below:

$$y_i \geq \frac{1}{w \cdot x_i + b}, (i=1, 2, \ldots, n) \quad (10)$$

Accordingly, when Equations 9 and 10 are combined, Equation 11 below is obtained for all vectors ($x_i \in S$).

$$y_i d_i \geq \frac{1}{\|w\|} \quad (11)$$

Thus, $$\frac{1}{\|w\|}$$

becomes a lower bound among distances between the vector ($x_i$) and the separating hyperplanes (w, b).

$$\frac{2}{\|w\|},$$

a measurement value for a distance between two classes in "w" direction, is called a margin.

Assumed is that there is a set (D) of data with a linear equation as expressed in Equation 12 below:

$$D=(x_1, y_1), (x_1, y_2), \ldots, (x_i, y_i), i=1, 2, \ldots, n, n: \text{integer} \quad (12)$$

where, $x \in R^n$ and $y \in R$.

An optimal regression equation for $f(x)=(w \cdot x_i + b)$ can be obtained by minimizing a value of Equation 13 below:

$$\Phi(w, \varepsilon) = \frac{1}{2}|w|^2 + C\sum_{i=1}^{N} (\varepsilon_i^- + \varepsilon_i^+) \quad (13)$$

In Equation 13, "C" is a limit value and $\epsilon_i^+$, $\epsilon_i^-$ are margin variables representing upper and lower limits for a result of a specific system. For example, when considering in association with FIG. 3, $\epsilon_i^+$ can correspond to an upper limit value and $\epsilon_i^-$ can correspond to a lower limit value. An $\epsilon^-$ intensive loss function $L_\epsilon(y)$ can be expressed in Equation 14 below:

$$L_\varepsilon(y) = \begin{cases} 0 & \text{for } |f(x) - y| < \varepsilon \\ |f(x) - y| - \varepsilon & \text{otherwise} \end{cases} \quad (14)$$

In Equation 14, $\epsilon^-$ intensive regression can be calculated in Equation 15 below:

$$\max_{\alpha, \alpha^*} W(\alpha, \alpha^*) = \max_{\alpha, \alpha^*} -\frac{1}{2}\sum_{i=1}^{p}\sum_{j=1}^{p}(\alpha_i - \alpha_i^*)(\alpha_j - \alpha_j^*)\langle x_i, x_j \rangle + \quad (15)$$

$$\sum_{i=1}^{p} \alpha_i(y_i - \varepsilon) - \alpha_i^*(y_i + \varepsilon)$$

Here, when Equation 15 has a constraint below, $$0 \leq \alpha_i, \alpha_i^* \leq C, \; p = \text{natural number} \quad (16)$$

$$\sum_{i=1}^{p}(\alpha_i - \alpha_i^*) = 0$$

a regression equation 17 below is given from Equations 15 and 16.

$$w' = \sum_{i=1}^{p}(\alpha_i - \alpha_i^*)x_i \quad (17)$$

$$b' = -\frac{1}{2}\langle w', x_s \rangle$$

Here, <w', b'> correspond to saddle points of a function expressed in Equations below. "$x_s$" denotes data values at the saddle points.

A basic concept of nonlinear regression starts from a nonlinear expansion of high-dimensional data. Thus, Lagrangian variables $\alpha_i$ and $\alpha_i^*$ for the $\epsilon^-$ intensive loss function can be determined in Equations 18 and 19 below:

$$L = \frac{1}{2}w \cdot w - \sum_{i=1}^{N}\alpha_i[y_i(w \cdot x_i + b) - 1] \quad (18)$$

$$f(x) = \sum_{SVs}(\alpha_i' - \alpha_i'^*)K(x_i, x) + b \quad (19)$$

In Equation 19, $$\sum_{SVs}$$

means a sum of only support vectors. The support vector corresponds to $x_i$ in Equation 20 below:

$$\alpha_i'(y_i(w'\cdot x_i + b) - 1) = 0 \quad (20)$$

where, i: 1, 2, . . . , N (N: integer).

Also, in Equation 19, the function f(x) can be expressed as in Equation 21 below:

$$f(x) = \langle w', x \rangle = \Sigma(\alpha_i' - \alpha_i'^*)K(x_i, x) + b \quad (21)$$

Thus, b' can be expressed by Equations 17 and 21 as in Equation 22 below:

$$b' = -\frac{1}{2}\sum_{i=1}^{p}(\alpha_i' - \alpha_i'^*)(K(x_i, x_r) + K(x_i, x_s)) \quad (22)$$

The use of the nonlinear regression equation can lead to an excellent performance of nonlinearly estimating a total amount with a small amount of data.

The SVM 140 periodically outputs a prediction product value ($Y_T$) on the basis of part of the process OES data (POES1(1) to POESN(M)) selected on the basis of the reference ranking values ($\lambda_R 1$ to $\lambda_R N$), part of the linear reference loading vectors ($A_R 1(1)$ to $A_R 1(N)$, $A_R 2(1)$ to $A_R 2(N)$, . . . , $A_R N(1)$ to $A_R N(N)$) additionally selected on the basis of the reference ranking values ($\lambda_R 1$ to $\lambda_R N$), and the nonlinear reference loading vectors ($A_{NR}1$ to $A_{NR}G$). For instance, it is assumed that the process OES data selected on the basis of the reference ranking values ($\lambda_R 1$ to $\lambda_R N$) are equal to POES1(1) to POES1(M), POES2(1) to POES2(M), and POES3(1) to POES3(M) (corresponding to wavelengths (X1, X2, and X3)). When assuming that the linear reference loading vectors sequentially selected on the basis of the rate values ($R_R 1$ to $R_R N$) and the reference ranking values ($\lambda_R 1$ to $\lambda_R N$) are equal to $A_R 1(1)$ to $A_R 1(3)$, the prediction product value ($Y_T$) can be expressed in Equation 23 below:

$$Y_T = A_R 1(1) \cdot X1 + A_R 1(2) \cdot X2 + \quad (23)$$
$$A_R 1(3) \cdot X3 + A_{NR}1 \cdot X1^2 + A_{NR}2 \cdot X2^2 + A_{NR}3 \cdot X3^2 +$$
$$A_{NR}4 \cdot X1 \cdot X2 + A_{NR}5 \cdot X2 \cdot X3 + A_{NR}6 \cdot X3 \cdot X1$$

In Equation 23, one-dimensional (that is, linear) functions (X1, X2, and X3) and two-dimensional (that is, nonlinear) functions ($X1^2$, $X2^2$, $X3^2$, X1·X2, X2·X3, and X3·X1) represent the process OES data (e.g., POES1(1) to POES3(1)) sampled at the same sampling time (e.g., a sampling time (t1)) among the selected process OES data (part of POES1(1) to POES3(M)). Here, the number of nonlinear functions is equal to the number of the nonlinear reference loading vectors ($A_{NR}1$ to $A_{NR}G$).

The SVM 140 periodically outputs the prediction product value ($Y_T$) on the basis of the process OES data sampled once every sampling time. Likely the actual product value ($Y_P$) described above, the prediction product values ($Y_T$) periodically output from the SVM 140 with the lapse of time form one waveform (W1) as shown in FIG. 6. In FIG. 6, the reason why a slight interval between the waveform (W1) formed by the prediction product values ($Y_T$) and the waveform (W2) formed by the actual product values ($Y_P$) occurs is that with the progress of a process, an etch by-product generated within the plasma reaction chamber leads to pollution of a window 311 (FIG. 4) provided at an outer wall of the plasma reaction chamber.

In more detail, the SVM 140 real-time outputs the prediction product values ($Y_T$) during the process wafer etch or deposition process on the basis of the linear and nonlinear reference loading vector values that are generated during the reference wafer etch or deposition process. However, the product generator 130 outputs the actual product values ($Y_P$) on the basis of the linear process loading vector value generated during the process wafer etch or deposition process, after the process wafer etch or deposition process is terminated or not in real time but while the process wafer etch or deposition process is executed, because the actual product value ($Y_P$), a value for determining normality or abnormality of the process wafer afterwards, is not needed in real time. Thus, a pollution level of the window 311 provided at the outer wall of the plasma reaction chamber increases more under environments (that is, under internal environments of the plasma reaction chamber during execution of the process wafer etch or deposition process) of when the product generator 130 outputs the actual product value ($Y_P$) than under environments (that is, an internal environment of the plasma reaction chamber during execution of the reference wafer etch or deposition process) of when the SVM 140 outputs the prediction product values ($Y_T$). The pollution of the window 311 as above leads to weakness of an intensity of lights emitted outside the plasma reaction chamber through the window 311, causing a slight error of the process OES data values. However, an interval between the waveforms (W1 and W2) does not have so much influence on detecting the etch endpoint (E) in the endpoint determiner 150 because a curve of the waveform (W1) formed by the prediction product values ($Y_T$) and a curve of the waveform (W2) formed by the actual product values ($Y_P$) are equal to each other as shown in FIG. 6.

In Equation 23, the prediction product value ($Y_T$) is expressed only with one-dimensional functions and two-dimensional functions; however, an equation for calculating the prediction product value ($Y_T$) can more include more-dimensional nonlinear functions. Also, for description convenience, Equation 23 expresses the prediction product value ($Y_T$) when three wavelengths are selected on the basis of the reference ranking values ($\lambda_R 1$ to $\lambda_R N$); however, the number of functions included in the equation defining the prediction product value ($Y_T$) also increases in proportion as the number of selected wavelengths increases. For example, when the reference ranking values represent 3000 ranks (that is, there are $\lambda_R 1$ to $\lambda_R 3000$) and a rank preset to the data selector 120 is a high rank 10%, the data selector 120 selects the process OES data corresponding to 300 wavelengths. At this time, the number of one-dimensional functions included in the equation defining the prediction product value ($Y_T$) is equal to 300.

As described above, when the etch or deposition endpoint of the process wafer is detected on the basis of the prediction product value ($Y_T$) calculated using the linear and nonlinear functions, despite the fact that the prediction product value ($Y_T$) is calculated using only a partial wavelength, the detection result is similar with a result of when the etch or deposition endpoint is detected, as it were, considering a whole wavelength.

Figure 7:
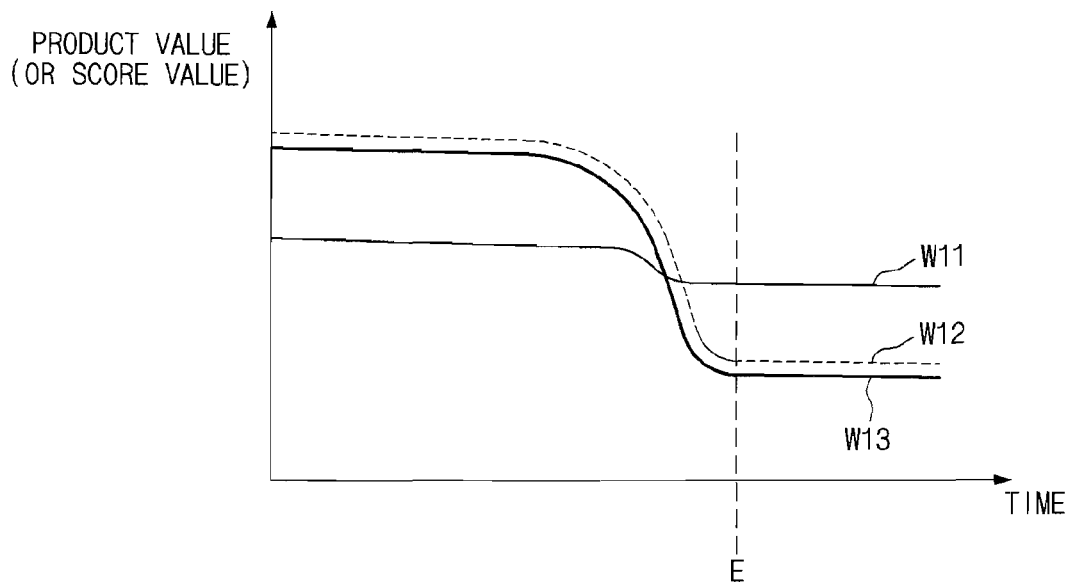
FIG. 7 is a graph showing a waveform formed by prediction product values of FIG. 2 and waveforms formed by score values.

Referring to FIG. 7, "W11" denotes a waveform formed by score values periodically obtained by PCA processing only OES data corresponding to several wavelengths of significance. Here, the score value is a result value obtained by multiplying normalized OES data by a linear loading vector value. "W12" denotes a waveform formed by score values periodically obtained by PCA processing all OES data corresponding to a whole wavelength. "W13" denotes a waveform formed by prediction product values periodically obtained by computing OES data corresponding to a partial wavelength (e.g., 20% of a whole wavelength) with the linear and nonlinear reference loading vector values. Because a difference between score values before and after an etch endpoint (E) is very small, it is very difficult to distinguish the etch endpoint (E) on the basis of the waveform (W12). Compared to the waveform (W12), the waveform (W13) can clearly show an etch endpoint (E) because a difference between product values before and after the etch endpoint (E) is relatively large.

Whenever the process wafer etch or deposition process is executed, the SVM 140 accumulates each of the actual product values ($Y_P$) received from the product generator 130 and calculates an average value (AVR) and a mean deviation value (MDV) for the accumulated actual product values ($Y_P$). The MDV can be expressed in Equation 24 below:

$$MDV = \left| Y_{P(n,j)} - \frac{\sum_{i=k}^{n-1} Y_{i,j}}{n-k} \right| \quad (24)$$

where, $Y_{P(n,j)}$: actual product value at j-th sampling time during n-th wafer etch or deposition process, and $\sum_{i=k}^{n-1} Y_{i,j}$:

average value (AVR) after execution of k-th wafer etch or deposition process.

The endpoint determiner 150 analyzes a waveform (W1) formed by prediction product values ($Y_T$) periodically received from the SVM 140, detects an etch or deposition endpoint (E) of a corresponding process wafer, and outputs a detection signal (EPD).

Figure 9:
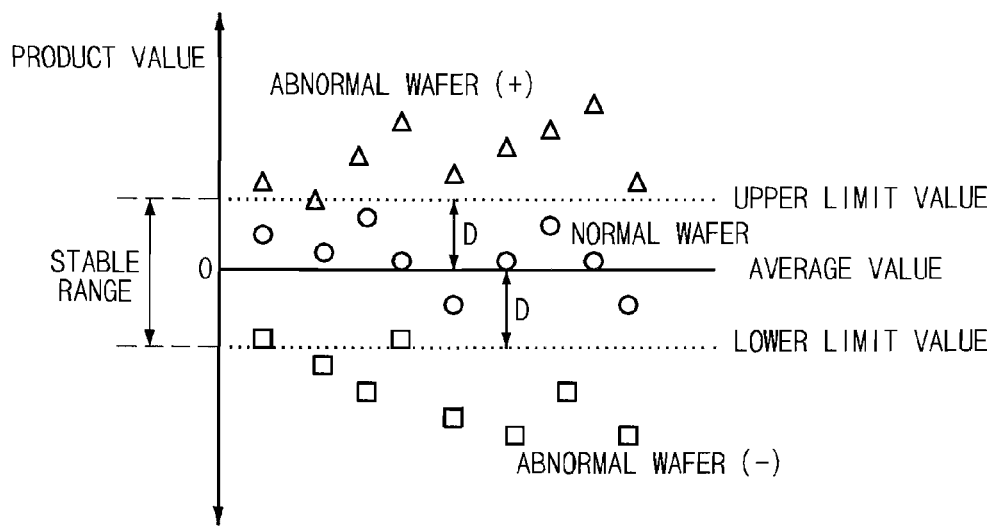
FIG. 9 is a graph illustrating a distribution of values associated with an abnormality diagnosis operation of the endpoint detection device of FIG. 2.

The abnormality diagnosis unit 160 determines normality or abnormality of a currently etched or deposited process wafer depending on whether a mean deviation value (MDV) received from the SVM 140 is included within a stable range (Referring to FIG. 9) determined by an average value (AVR). Here, an upper limit value of the stable range is determined by a sum of the average value (AVR) and a deviation value (D). A lower limit value of the stable range is determined by a difference between the average value (AVR) and the deviation value (D). The user can preset the deviation value (D) to the abnormality diagnosis unit 160 through the input unit 360 (FIG. 14). In detail, if the user inputs a deviation value (D) to be preset through the input unit 360, the input unit 360 outputs a set signal (SET) and the abnormality diagnosis unit 160 sets the deviation value (D) in response to the set signal (SET).

The abnormality diagnosis unit 160 outputs a display control signal (DCTL) such that the display unit 101 visually displays normality or abnormality of a process wafer depending on a result of determining whether the mean deviation value (MDV) is included within the stable range. Here, the display unit 101 corresponds to a display unit 350 of FIG. 14.

Operation of the endpoint detection device 100 is all described in detail below. For description convenience, the description is made centering on a process of detecting an etch endpoint upon execution of a wafer etch process. FIG. 5 is a conceptual diagram illustrating a whole operation process of the endpoint detection device of FIG. 2.

Figure 5:
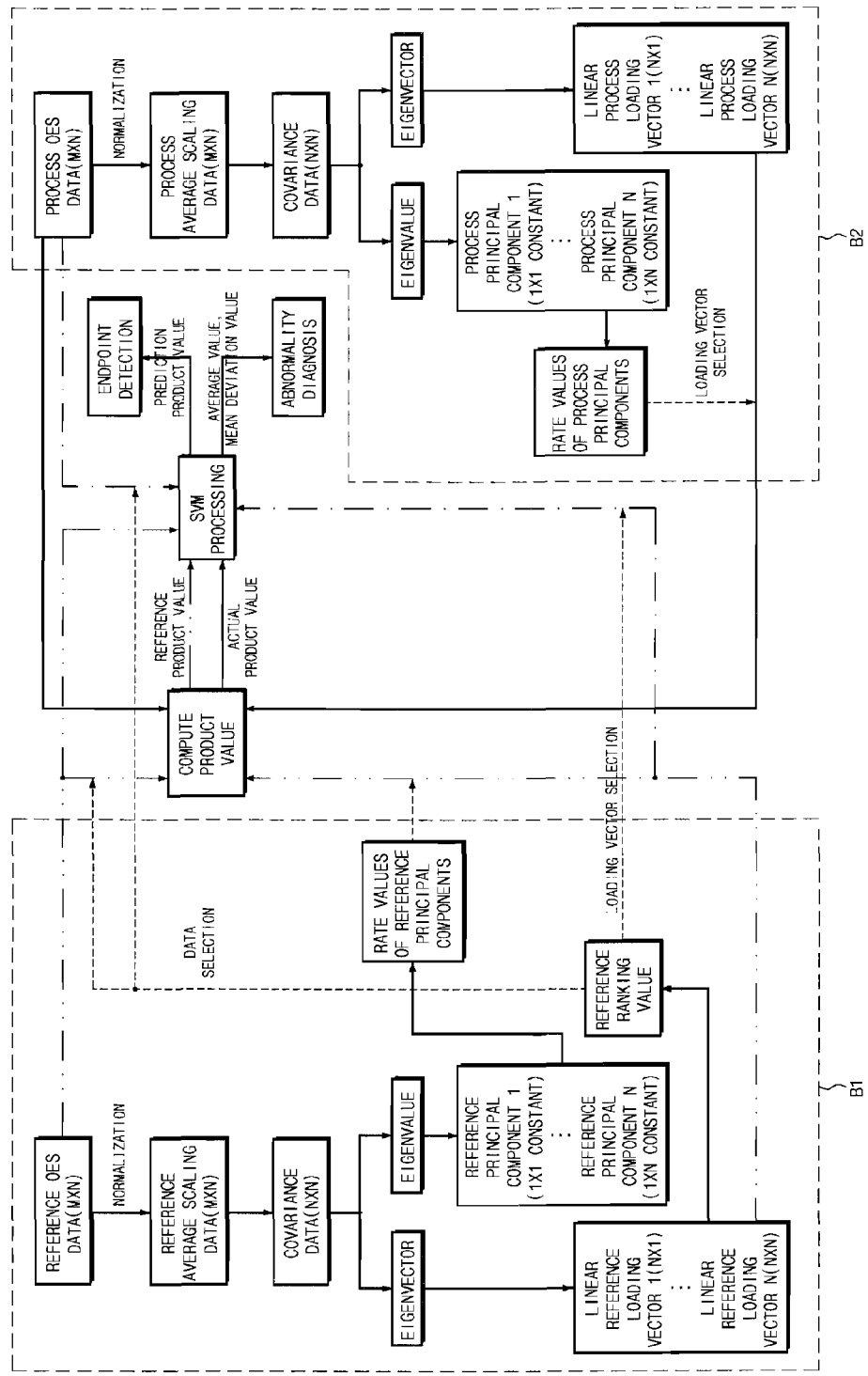
FIG. 5 is a conceptual diagram illustrating a whole operation process of the endpoint detection device of FIG. 2.

First, in order to make the SVM 140 learn, the OES data operation unit 110 carries out an operation as shown by a dotted-line box (B1) of FIG. 5.

During the reference wafer etch process, the spectrometer 330 samples first lights of a whole wavelength emitted from the inside of the plasma reaction chamber 310 at each sampling time and converts the sampled first lights into reference OES data (ROES1(1) to ROESN(M)). The normalization processor 111 normalizes the reference OES data (ROES1(1) to ROESN(M)) and outputs reference average scaling data (RASD1(1) to RASDN(M)). The PCA processor 112 PCA processes the reference average scaling data (RASD1(1) to RASDN(M)) and outputs rate values ($R_R 1$ to $R_R N$) of reference principal components (PC1 to PCN) (N: integer indicative of the number of wavelengths) and linear reference loading vectors ($A_R 1(1)$ to $A_R 1(N)$, $A_R 2(1)$ to $A_R 2(N)$, . . . , $A_R N(1)$ to $A_R N(N)$). The ranking determiner 113 outputs reference ranking values ($\lambda_R 1$ to $\lambda_R N$) (N: the number of wavelengths) on the basis of the linear reference loading vectors ($A_R 1(1)$ to $A_R 1(N)$, $A_R 2(1)$ to $A_R 2(N)$, . . . , $A_R N(L)$ to $A_R N(N)$). The storage unit 114 stores the linear reference loading vectors ($A_R 1(1)$ to $A_R 1(N)$, $A_R 2(1)$ to $A_R 2(N)$, . . . , $A_R N(L)$ to $A_R N(N)$) received from the PCA processor 112 and the rate values ($R_R 1$ to $R_R N$) of the reference principal components (PC1 to PCN) and stores the reference ranking values ($\lambda_R 1$ to $\lambda_R N$) received from the ranking determiner 113.

After that, the data selector 120 selects part of the linear reference loading vectors ($A_R1(1)$ to $A_R1(N)$, $A_R2(1)$ to $A_R2(N)$, ..., $A_RN(1)$ to $A_RN(N)$) on the basis of the rate values ($R_R1$ to $R_RN$). In this exemplary embodiment, for description convenience, a case that the linear reference loading vectors selected by the data selector 120 are equal to $A_R1(1)$ to $A_R1(N)$ corresponding to a reference principal component (PC1) is described for example. The data selector 120 outputs the selected linear reference loading vectors ($A_R1(1)$ to $A_R1(N)$) to the product generator 130. The product generator 130 periodically outputs a reference product value ($Y_R(U)$) to the SVM 140 by applying the linear reference loading vectors ($A_R1(1)$ to $A_R1(N)$) and the reference OES data (ROES1(1) to ROESN(M)) to Equation 6.

While the product generator 130 outputs the reference product value ($Y_R(U)$), the data selector 120 selects part of the reference OES data (ROES1(1) to ROESN(M)) on the basis of the reference ranking values ($\lambda_R1$ to $\lambda_RN$) and outputs the selected reference OES data to the SVM 140. In this exemplary embodiment, for description convenience, a case that reference OES data selected by the data selector 120 are equal to ROES1(1) to ROES1(M), ROES2(1) to ROES2(M), and ROES3(1) to ROES3(M) corresponding to wavelengths (X1, X2, and X3) is described for example. The SVM 140 performs regression on the basis of the reference product value ($Y_R(U)$) and the reference OES data (ROES1(1) to ROES1(M), ROES2(1) to ROES2(M), and ROES3(1) to ROES3(M)) and generates nonlinear reference loading vectors ($A_{NR}1$ to $A_{NR}6$).

After the SVM 140 completes the regression, a process wafer etch process is executed. During the process wafer etch process, the spectrometer 330 converts second lights of a whole wavelength emitted from the inside of the plasma reaction chamber 310 into process OES data (POES1(1) to POESN(M)) at each sampling time. The data selector 120 selects part of the process OES data (POES1(1) to POESN(M)) on the basis of the reference ranking values ($\lambda_R1$ to $\lambda_RN$) and outputs the selected process OES data to the SVM 140. Like selecting the reference OES data, the data selector 120 selects the process OES data (POES1(1) to POES1(M), POES2(1) to POES2(M), and POES3(1) to POES3(M)) corresponding to the wavelengths (X1, X2, and X3).

Next, the SVM 140 periodically outputs a prediction product value ($Y_T$) by applying the linear reference loading vectors ($A_R(1)$ to $A_R1(N)$), the nonlinear reference loading vectors ($A_{NR}1$ to $A_{NR}6$), and the process OES data (POES1(1) to POES1(M), POES2(1) to POES2(M), and POES3(1) to POES3(M)) to Equation 23. The endpoint determiner 150 analyzes a waveform (W1) formed by the prediction product values ($Y_T$) periodically received from the SVM 140, detects an etch or deposition endpoint (E) of a corresponding process wafer, and outputs a detection signal (EPD).

In order to determine whether abnormality occurs during the process wafer etch process, the OES data operation unit 110 carries out an operation to calculate an actual product value ($Y_P$) as shown by a dotted-line box (B2) of FIG. 5. First, the normalization processor 111 normalizes the process OES data (POES1(1) to POESN(M)) and outputs the process average scaling data (PASD1(1) to PASDN(M)). The PCA processor 112 PCA processes the process average scaling data (PASD1(1) to PASDN(M)) and outputs rate values ($R_P1$ to $R_PN$) of process principal components (PC1 to PCN) (N: integer indicative of the number of wavelengths) and linear process loading vectors ($A_P1(1)$ to $A_P1(N)$, $A_P2(1)$ to $A_P2(N)$, ..., $A_PN(1)$ to $A_PN(N)$). The ranking determiner 113 outputs process ranking values ($\lambda_P1$ to $\lambda_PN$) (N: the number of wavelengths) on the basis of the linear process loading vectors ($A_P1(1)$ to $A_P1(N)$, $A_P2(1)$ to $A_P2(N)$, ..., $A_PN(1)$ to $A_PN(N)$). The storage unit 114 stores the linear process loading vectors ($A_P1(1)$ to $A_P1(N)$, $A_P2(1)$ to $A_P2(N)$ ... $A_PN(1)$ to $A_PN(N)$) and the rate values ($R_P1$ to $R_PN$) of the process principal components (PC1 to PCN) received from the PCA processor 112 and stores the process raking values ($\lambda_P1$ to $\lambda_PN$) received from the ranking determiner 113.

After that, the data selector 120 selects part of the linear process loading vectors ($A_P1(1)$ to $A_P1(N)$, $A_P2(1)$ to $A_P2(N)$, ..., $A_PN(1)$ to $A_PN(N)$) on the basis of the rate values ($R_P1$ to $R_PN$). In this exemplary embodiment, for description convenience, a description is made for an exemplary case that the linear process loading vectors selected by the data selector 120 are equal to $A_P1(1)$ to $A_P1(N)$ corresponding to the process principal component (PC1). The product generator 130 periodically outputs the actual product value ($Y_P$) to the SVM 140 by applying the linear process loading vectors ($A_P1(1)$ to $A_P1(N)$) and the process OES data (POES1(1) to POESN(M)) to Equation 6.

The SVM 140 accumulates each of the actual product values ($Y_P$) and calculates an average value (AVR) and a mean deviation value (MDV) by applying the accumulated actual product values ($Y_P$) to Equation 24. The abnormality diagnosis unit 160 visually displays normality or abnormality of a currently etched or deposited process wafer through the display unit 101 depending on whether the mean deviation value (MDV) received from the SVM 140 is included within a stable range (Referring to FIG. 9) determined by the average value (AVR).

Meantime, with consecutive progress of the process wafer etch process, a change of an etch process condition within the plasma reaction chamber 310 can occur. Thus, as in FIG. 8, there is a need to update the linear and nonlinear reference loading vector values learned by the SVM 140 and required for generating the prediction product value. The data selector 120 outputs an update request signal (UPDATE) to the SVM 140 when the process wafer etch process is executed by the set number of times.

Like the above-described process, a process for making the SVM 140 learn using the process OES data (POES1(1) to POESN(M)), the rate values ($R_P1$ to $R_PN$) of the process principal components, the linear process loading vectors ($A_P1(1)$ to $A_P1(N)$, $A_P2(1)$ to $A_P2(N)$, ..., $A_PN(1)$ to $A_PN(N)$), and the process ranking values ($\lambda_P1$ to $\lambda_PN$), which are obtained as a result of operation of the OES data operation unit 110 for calculating the actual product value ($Y_P$), is executed. As a result, the SVM 140 learns new linear and nonlinear process loading vector values that are used to generate a prediction product value for detecting an etch endpoint of a subsequent process wafer.

Figure 8:
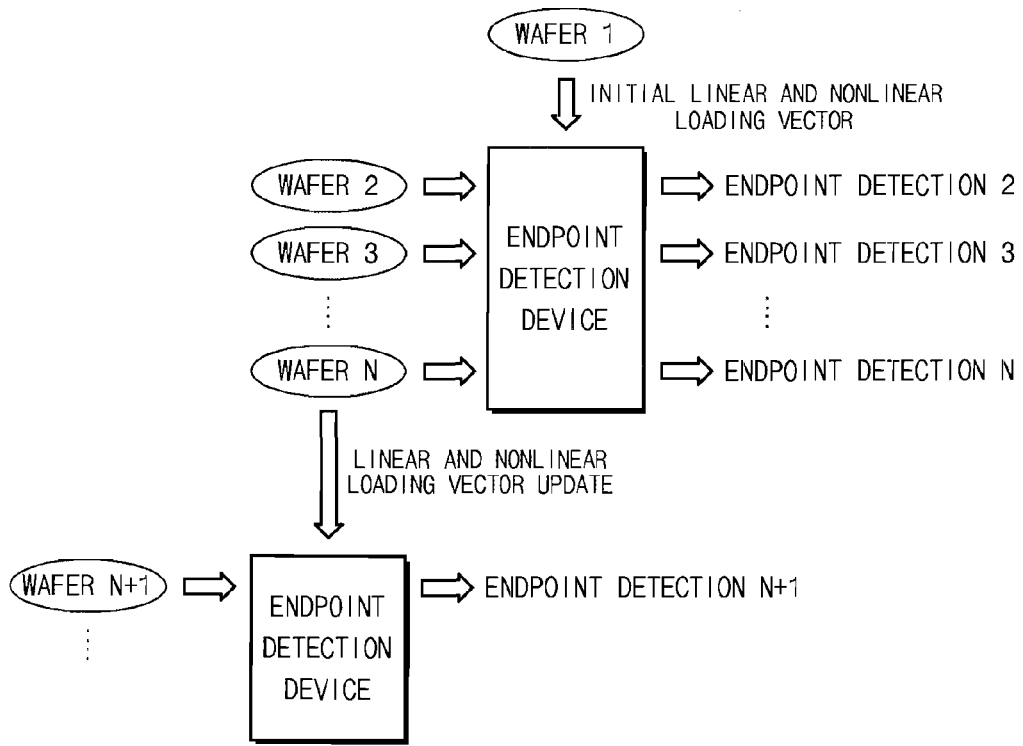
FIG. 8 is a diagram illustrating a process of updating linear and nonlinear loading vectors in a Support Vector Machine (SVM) of FIG. 2.

Referring to FIG. 8, the SVM 140 uses initial linear and nonlinear loading vectors generated by a first etched wafer 1 to generate prediction product values for wafers 2 to N. After that, the SVM 140 uses linear and nonlinear loading vectors generated during an etch process of the wafer N to generate prediction product values for wafers (starting from an (N+1)-th wafer) subsequent to the wafer N.

Figure 10:
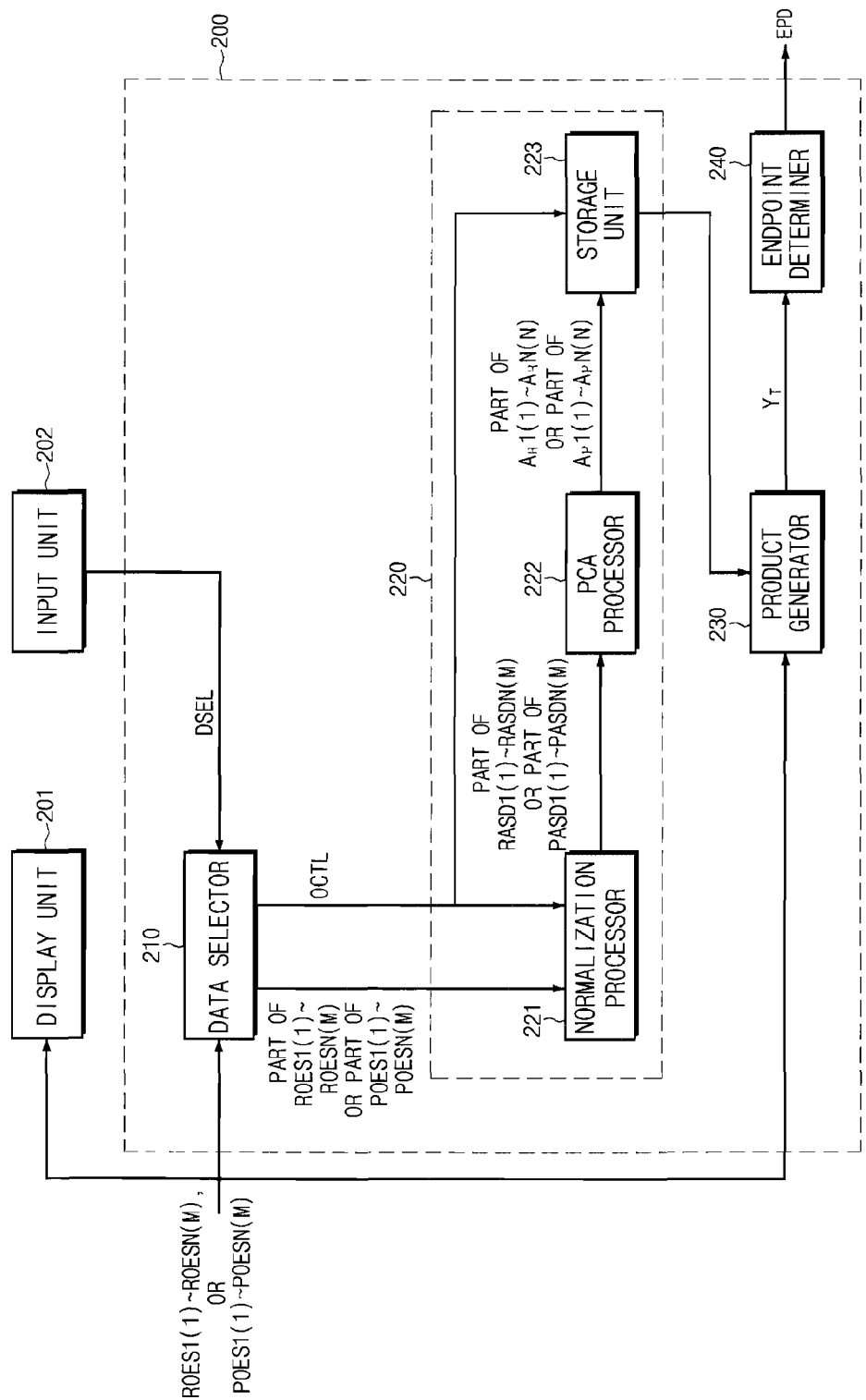
FIG. 10 is a block diagram illustrating a detail of an endpoint detection device according to another exemplary embodiment of the present invention.

FIG. 10 is a block diagram illustrating a detail of an endpoint detection device according to another exemplary embodiment of the present invention. Construction and detailed operation of the endpoint detection device 200 are similar with those of the above-described endpoint detection device 100. A difference between the endpoint detection devices 200 and 100 is that the endpoint detection device 200 excludes an SVM and an abnormality diagnosis unit.

Referring to FIG. 10, the endpoint detection device 200 includes a data selector 210, an OES data operation unit 220, a product generator 230, and an endpoint determiner 240.

The data selector 210 sets a data selection range in response to a data selection signal (DSEL) received from an input unit 202. The input unit 202 corresponds to the input unit 360 of FIG. 14 and includes a plurality of keys. The input unit 202 outputs a data selection signal (DSEL) in response to pressing of the plurality of keys. The data selector 210 outputs an operation control signal (OCTL) in response to the data selection signal (DSEL). The data selector 210 selects part of reference OES data (ROES1(1) to ROESN(M)) on the basis of a preset data selection range during a reference wafer etch or deposition process. The data selection range of the data selector 210 can be any one or more of at least one set wavelength band range, at least one set time range, and a wavelength band range of lights emitted by at least one set element. This is described in more detail below with reference to FIGS. 11 to 13.

Figure 11:
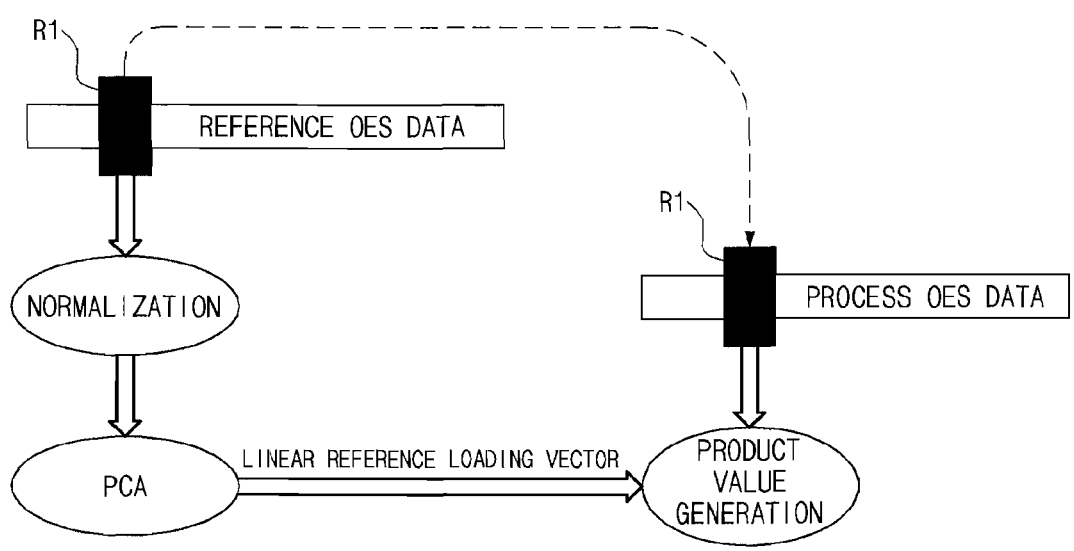
FIGS. 11 to 13 are diagrams illustrating a data selection range set to a data selector of FIG. 10.
Figure 12:
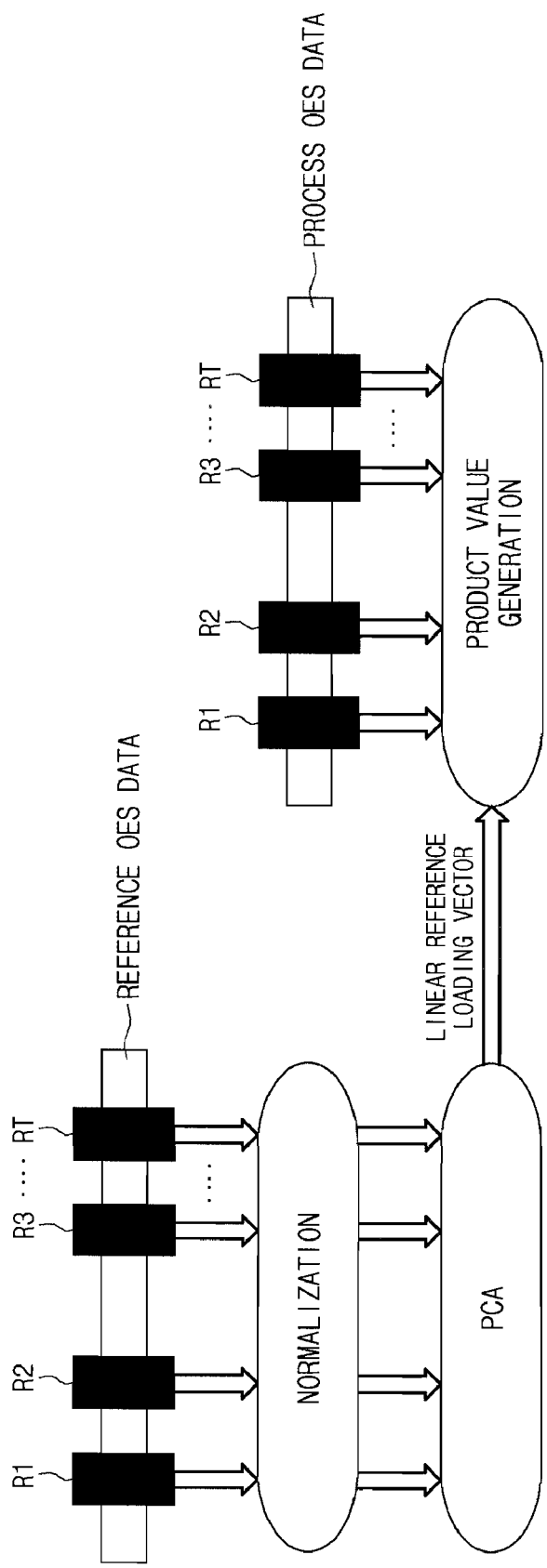
Figure 13:
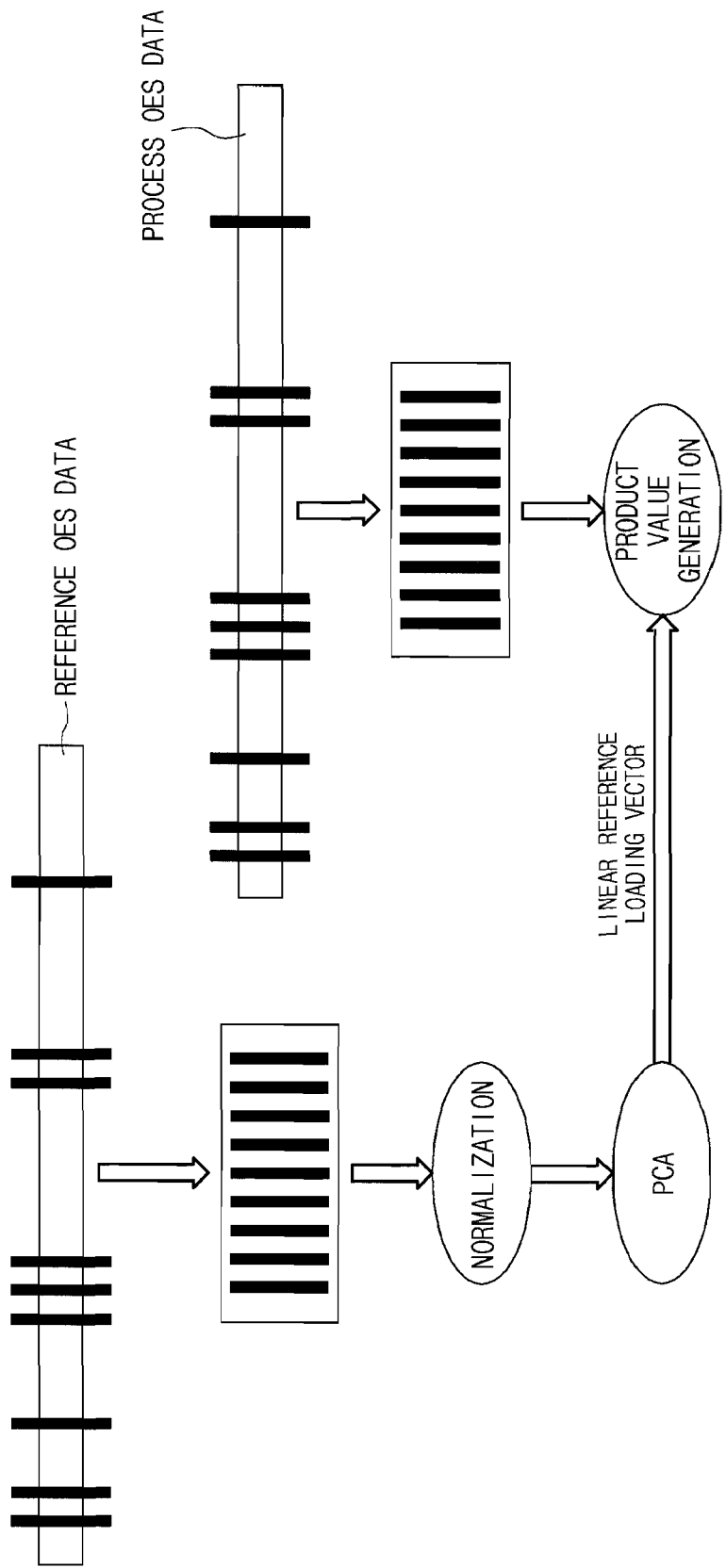

Referring first to FIG. 11, the data selector 210 selects all reference OES data and process OES data included within one set wavelength band range (or one set time range) (R1), respectively. Referring to FIG. 12, the data selector 210 selects all reference OES data and process OES data included within a plurality of set wavelength band ranges (or a plurality of set time range (R1 to RT) (T: integer)), respectively. Referring to FIG. 13, the data selector 210 can select reference OES data and process OES data, respectively, into which the spectrometer 330 converts first and second light(s) of a wavelength emitted by at least one set element among first and second lights of a whole wavelength emitted from the inside of a plasma reaction chamber 310. The first or second light emitted by at least one set element can be distributed over a plurality of wavelength bands.

The OES data operation unit 220 includes a normalization processor 221, a PCA processor 222, and a storage unit 223. The normalization processor 221 and the storage unit 223 operate in response to an operation control signal (OCTL), respectively. Detailed operation of the normalization processor 221 and the PCA processor 222 are similar with those of the normalization processor 111 and the PCA processor 112 and therefore, their detailed description is omitted.

The product generator 230 periodically outputs a prediction product value ($Y_T$) by applying the linear reference loading vectors (part of $A_R1(1)$ to $A_R1(N)$, $A_R2(1)$ to $A_R2(N)$, ..., $A_RN(1)$ to $A_RN(N)$) received from the storage unit 223 and the process OES data (part of POES1(1) to POESN(M)) selected by the data selector 210 to Equation 6. The endpoint determiner 240 detects a process wafer etch or deposition endpoint on the basis of the periodically received prediction product value ($Y_T$) and outputs a detection signal (EPD).

Operation of the endpoint detection device 200 is described in more detail below. For description convenience, the description is made centering on operation of the endpoint detection device 200 upon execution of a wafer etch process. During a reference wafer etch process, the spectrometer 330 samples first lights of a whole wavelength emitted from the inside of the plasma reaction chamber 310 at each sampling time and converts the sampled lights into reference OES data (ROES1(1) to ROESN(M)). A display unit 201 displays the reference OES data (ROES1(1) to ROESN(M)) in a three-dimensional graphic picture. A user identifies an event zone from a graphic picture displayed on the display unit 201 and sets a data selection range corresponding to the event zone to the data selector 210 through the input unit 202.

After that, the data selector 210 outputs an operation control signal (OCTL) and selects part of the reference OES data (ROES1(1) to ROESN(M)) on the basis of the set data selection range. The normalization processor 221 normalizes the reference OES data (part of ROES1(1) to ROESN(M)) received from the data selector 210 in response to the operation control signal (OCTL) and outputs reference average scaling data (part of RASD1(1) to RASDN(M)). The PCA processor 222 PCA processes the reference average scaling data (part of RASD1(1) to RASDN(M)) and outputs linear reference loading vectors (part of $A_R1(1)$ to $A_R1(N)$, $A_R2(1)$ to $A_R2(N)$, ..., $A_RN(1)$ to $A_RN(N)$). The storage unit 223 stores the linear reference loading vectors (part of $A_R1(1)$ to $A_R1(N)$, $A_R2(1)$ to $A_R2(N)$, ..., $A_RN(1)$ to $A_RN(N)$) received from the PCA processor 222, in response to the operation control signal (OCTL).

After that, during a process wafer etch or deposition process, the data selector 210 selects part of the process OES data (POES1(1) to POESN(M)) on the basis of the data selection range. The product generator 230 periodically outputs a prediction product value ($Y_T$) by applying the linear reference loading vectors (part of $A_R1(1)$ to $A_R1(N)$, $A_R2(1)$ to $A_R2(N)$, ..., $A_RN(1)$ to $A_RN(N)$) received from the storage unit 223 and the process OES data (part of POES1(1) to POESN(M)) received from the data selector 210 to Equation 6. The endpoint determiner 240 detects a process wafer etch or deposition endpoint on the basis of the periodically received prediction product values ($Y_T$) and outputs a detection signal (EPD).

Whenever the process wafer etch process is executed, the display unit 201 consecutively displays corresponding process OES data (POES1(1) to POESN(M)) in a three-dimensional graphic picture. The user monitors the graphic picture consecutively displayed on the display unit 201 and identifies a change or non-change of an event zone (e.g., a zone where much meander occurs). Here, the change of the event zone represents a change of an etch condition within the plasma reaction chamber 310. Thus, when the event zone changes, the user can change the data selection range of the data selector 210 through the input unit 202 to update the linear reference loading vector stored in the storage unit 223. The input unit 202 outputs a data selection signal (DSEL) to the data selector 210 in response to user's pressing a key. The data selector 210 resets the data selection range in response to the data selection signal (DSEL).

After that, the data selector 210 and the OES data operation unit 220 operate like the above description. The storage unit 223 stores a new linear process loading vector value. For example, when the user sets a new data selection range of the data selector 210 during an N-th process wafer etch process, the storage unit 223 stores a linear process loading vector value obtained as a result of the N-th process wafer etch process. After that, the product generator 230 uses the linear process loading vector updated in the storage unit 223 from when an (N+1)-th process wafer etch process is executed to generate a prediction product value ($Y_T$).

FIG. 14 is a block diagram schematically illustrating a plasma reactor including an endpoint detection device according to the present invention. Referring to FIG. 14, the plasma reactor 300 includes a plasma reaction chamber 310, an optical fiber cable 320, a spectrometer 330, an endpoint detection device 100 or 200, a plasma reaction controller 340, the display unit 350, and an input unit 360.

A reference wafer or a process wafer is mounted within the plasma reaction chamber 310. The optical fiber cable 320 collects whole wavelength lights emitted from the inside of the plasma reaction chamber 310 through a window 311 provided at an outer wall of the plasma reaction chamber 310 and forwards the collected lights to the spectrometer 330 during a reference wafer or process wafer etch or deposition process. The spectrometer 330 converts the whole wavelength lights emitted from the inside of the plasma reaction chamber 310 into reference OES data (ROES1(1) to ROESN(M)) during the reference wafer etch or deposition process. The spectrometer 330 converts the whole wavelength lights emitted from the inside of the plasma reaction chamber 310 into process OES data (POES1(1) to POESN(M)) during the process wafer etch or deposition process. The reference wafer etch or deposition process is performed before the process wafer etch or deposition process. That is, after a reference wafer is etched or deposited once, a plurality of process wafers are etched or deposited in a consecutive manner. The endpoint detection device 100 or 200 detects an etch or deposition endpoint of the process wafer on the basis of the reference OES data (ROES1(1) to ROESN(M)) and the process OES data (POES1(1) to POESN(M)) and outputs a detection signal (EPD). Construction and detailed operation of the endpoint detection device 100 or 200 are substantially the same as the above description and thus, its detailed description is omitted. The plasma reaction controller 340 changes etch or deposition condition within the plasma reaction chamber 310 in response to the detection signal (EPD). The display unit 350 visually displays normality or abnormality of the etched or deposited process wafer or displays the reference OES data (ROES1(1) to ROESN(M)) or the process OES data (POES1(1) to POESN(M)) in a three-dimensional graphic picture, under the control of the endpoint detection device 100 or 200. A user inputs a variety of set values for controlling operation of the endpoint detection device 100 or 200 through the input unit 360.

As described above, in the endpoint detection device, the plasma reactor including the endpoint detection device, and the endpoint detection method according to the present invention, with execution of the real-time process wafer etch or deposition process, OES data is computed with loading vectors previously calculated during a previous etch or deposition process without real-time normalizing OES data generated in real time, and a product value for determining an etch or deposition endpoint is generated. Consequently, an endpoint detection speed can increase, thereby realizing the real-time control of the plasma reactor.

While the invention has been shown and described with reference to a certain preferred embodiment thereof, it will be understood by those skilled in the art that various changes in form and details may be made therein without departing from the spirit and scope of the invention as defined by the appended claims.

What is claimed is:

1. An endpoint detection device comprising:
   an Optical Emission Spectrometer (OES) data operation unit for processing reference OES data by normalization and Principal Component Analysis (PCA), outputting linear reference loading vectors and rate values of reference principal components, and outputting reference ranking values on the basis of the linear reference loading vectors;
   a data selector for first selecting part of the linear reference loading vectors on the basis of the rate values of the reference principal components, selecting part of the reference OES data or selecting part of process OES data on the basis of the reference ranking values, and second selecting part of the first selected linear reference loading vectors on the basis of the reference ranking values;
   a product generator for outputting at least one reference product value on the basis of the first selected linear reference loading vectors and the reference OES data;
   a Support Vector Machine (SVM) for performing regression on the basis of the selected reference OES data and the at least one reference product value, generating nonlinear reference loading vectors, and periodically outputting a prediction product value on the basis of the second selected linear reference loading vectors, the nonlinear reference loading vectors, and the selected process OES data; and
   an endpoint determiner for detecting a process wafer etch or deposition endpoint on the basis of the periodically received prediction product value and outputting a detection signal,
   wherein first lights of a whole wavelength emitted from the inside of a plasma reaction chamber are converted into the reference OES data by a spectrometer during a reference wafer etch or deposition process and second lights of a whole wavelength emitted from the inside of the plasma reaction chamber are converted into the process OES data by the spectrometer during a process wafer etch or deposition process executed after the reference wafer etch or deposition process,
   wherein the reference ranking values represent a ranking for the intensity of the first lights of the whole wavelength, and
   wherein the linear reference loading vectors each correspond to one-dimensional function values expressed by the reference OES data and the nonlinear reference loading vectors each correspond to S-dimensional, wherein S: integer larger than 1, function values expressed by the selected process OES data.

2. The device of claim 1, further comprising: an abnormality diagnosis unit for diagnosing normality or abnormality of a currently etched or deposited process wafer depending on whether a mean deviation value is comprised within a stable range determined by an average value and controlling a display unit to visually display the normality or abnormality of the process wafer,
   wherein the OES data operation unit processes the process OES data by normalization and PCA, further outputs linear process loading vectors and rate values of process principal components, and further outputs process ranking values representing a ranking for the intensity of the second lights of the whole wavelength on the basis of the linear process loading vectors,
   wherein the data selector selects part of the linear process loading vectors on the basis of the rate values of the process principal components,
   wherein the product generator further outputs an actual product value on the basis of the selected linear process loading vectors and the process OES data,
   wherein whenever the process wafer etch or deposition process is executed, the SVM accumulates each of the actual product values received from the product generator and further calculates the average value and the mean deviation value for the accumulated actual product values, and
   wherein the linear process loading vectors each correspond to one-dimensional function values expressed by the process OES data.

3. The device of claim 2, wherein when the number of times of execution of the process wafer etch or deposition process reaches the preset number of times, the data selector outputs an update request signal and further selects part of the process OES data and part of the selected linear process loading vectors on the basis of the process ranking values, the SVM performs regression on the basis of the actual product value generated by the product generator and the selected process OES data during a current process wafer etch or deposition process in response to the update request signal, generates nonlinear process loading vectors, and uses the further selected linear process loading vectors and the nonlinear process loading vectors to generate prediction product values from a time of a subsequent process wafer etch or deposition process up to a time of a process wafer etch or deposition process before execution of a subsequent regression operation, and the nonlinear reference loading vectors each correspond to S-dimensional (S: integer larger than 1) function values expressed by the selected process OES data.

4. The device of claim 2, wherein the OES data operation unit comprises:

a normalization processor for normalizing the reference OES data and outputting reference average scaling data or normalizing the process OES data and outputting process average scaling data;

a PCA processor for processing the reference average scaling data by PCA and outputting the linear reference loading vectors and the rate values of the reference principal components or processing the process average scaling data by PCA and outputting the linear process loading vectors and the rate values of the process principal components; and a ranking determiner for outputting the reference ranking values on the basis of the linear reference loading vectors or outputting the process ranking values on the basis of the linear process loading vectors.

5. The device of claim 4, wherein the OES data operation unit further comprises: a storage unit for storing the linear reference loading vectors and the rate values of the reference principal components or the linear process loading vectors and the rate values of the process principal components received from the PCA processor and storing the reference ranking values or the process ranking values received from the ranking determiner.

6. The device of claim 2, wherein an upper limit value of the stable range is determined by a sum of the average value and a deviation value, a lower limit value of the stable range is determined by a difference between the average value and the deviation value, and the deviation value is preset to the abnormality diagnosis unit.

7. A plasma reactor comprising:

a plasma reaction chamber which a reference wafer or a process wafer is mounted inside;

a spectrometer for converting first lights of a whole wavelength emitted from the inside of the plasma reaction chamber into reference OES data during a reference wafer etch or deposition process or converting second lights of a whole wavelength emitted from the inside of the plasma reaction chamber into process OES data during a process wafer etch or deposition process executed after the reference wafer etch or deposition process;

an optical fiber cable for collecting the first or second lights of the whole wavelength emitted from the inside of the plasma reaction chamber through a window provided at an outer wall of the plasma reaction chamber and forwarding the collected lights to the spectrometer during the reference wafer or process wafer etch or deposition process;

an endpoint detection device for detecting a process wafer etch or deposition endpoint and outputting a detection signal on the basis of the reference OES data and the process OES data; and a plasma reaction controller for controlling an etch or deposition condition within the plasma reaction chamber in response to the detection signal, the endpoint detection device comprising:

an OES data operation unit for processing the reference OES data by normalization and PCA, outputting linear reference loading vectors and rate values of reference principal components, and outputting reference ranking values on the basis of the linear reference loading vectors;

a data selector for first selecting part of the linear reference loading vectors on the basis of the rate values of the reference principal components, selecting part of the reference OES data or selecting part of the process OES data on the basis of the reference ranking values, and second selecting part of the first selected linear reference loading vectors on the basis of the reference ranking values;

a product generator for outputting at least one reference product value on the basis of the first selected linear reference loading vectors and the reference OES data;

an SVM for performing regression on the basis of the selected reference OES data and the at least one reference product value, generating nonlinear reference loading vectors, and periodically outputting a prediction product value on the basis of the second selected linear reference loading vectors, the nonlinear reference loading vectors, and the selected process OES data; and an endpoint determiner for detecting a process wafer etch or deposition endpoint on the basis of the periodically received prediction product value and outputting a detection signal, wherein the reference ranking values represent a ranking for the intensity of the first lights of the whole wavelength, and wherein the linear reference loading vectors each correspond to one-dimensional function values expressed by the reference OES data and the nonlinear reference loading vectors each correspond to S-dimensional, wherein S: integer larger than 1, function values expressed by the selected process OES data.

8. The plasma reactor of claim 7, further comprising: an abnormality diagnosis unit for diagnosing normality or abnormality of a currently etched or deposited process wafer depending on whether a mean deviation value is comprised within a stable range determined by an average value and controlling a display unit to visually display the normality or abnormality of the process wafer, wherein the OES data operation unit processes the process OES data by normalization and PCA, further outputs linear process loading vectors and rate values of process principal components, and further outputs process ranking values representing a ranking for the intensity of the second lights of the whole wavelength on the basis of the linear process loading vectors, wherein the data selector selects part of the linear process loading vectors on the basis of the rate values of the process principal components, wherein the product generator further outputs an actual product value on the basis of the selected linear process loading vectors and the process OES data, wherein whenever the process wafer etch or deposition process is executed, the SVM accumulates each of the actual product values received from the product generator and further calculates the average value and the mean deviation value for the accumulated actual product values, and wherein the linear process loading vectors each correspond to one-dimensional function values expressed by the process OES data.

9. The plasma reactor of claim 8, wherein when the number of times of execution of the process wafer etch or deposition process reaches the preset number of times, the data selector outputs an update request signal and further selects part of the process OES data and part of the selected linear process loading vectors on the basis of the process ranking values, the SVM performs regression on the basis of the actual product value generated by the product generator and the selected process OES data during a current process wafer etch or deposition process in response to the update request signal, generates nonlinear process loading vectors, and uses the further selected linear process loading vectors and the nonlinear process loading vectors to generate prediction product values from a time of a subsequent process wafer etch or deposition process up to a time of a process wafer etch or deposition process before execution of a subsequent regression operation, and the nonlinear reference loading vectors each correspond to S-dimensional (S: integer larger than 1) function values expressed by the selected process OES data.

10. The plasma reactor of claim 8, wherein the OES data operation unit comprises:

a normalization processor for normalizing the reference OES data and outputting reference average scaling data or normalizing the process OES data and outputting process average scaling data;

a PCA processor for processing the reference average scaling data by PCA and outputting the linear reference loading vectors and the rate values of the reference principal components or processing the process average scaling data by PCA and outputting the linear process loading vectors and the rate values of the process principal components; and a ranking determiner for outputting the reference ranking values on the basis of the linear reference loading vectors or outputting the process ranking values on the basis of the linear process loading vectors.

11. The plasmas reactor of claim 10, wherein the OES data operation unit further comprises: a storage unit for storing the linear reference loading vectors and the rate values of the reference principal components or the linear process loading vectors and the rate values of the process principal components received from the PCA processor and storing the reference ranking values or the process ranking values received from the ranking determiner.

12. An endpoint detection device comprising:

a data selector for setting a data selection range and outputting an operation control signal in response to a data selection signal, selecting part of reference OES data on the basis of the data selection range during a reference wafer etch or deposition process, and selecting part of process OES data on the basis of the data selection range during a process wafer etch or deposition process;

an OES data operation unit for processing the selected reference OES data by normalization and PCA and outputting linear reference loading vectors in response to the operation control signal;

a product generator for periodically outputting a prediction product value on the basis of the linear reference loading vectors and the selected process OES data; and an endpoint determiner for detecting a process wafer etch or deposition endpoint and outputting a detection signal on the basis of the periodically received prediction product value, wherein first lights of a whole wavelength emitted from the inside of a plasma reaction chamber are converted into the reference OES data by a spectrometer during a reference wafer etch or deposition process and second lights of a whole wavelength emitted from the inside of the plasma reaction chamber are converted into the process OES data by the spectrometer during a process wafer etch or deposition process executed after the reference wafer etch or deposition process, and wherein the linear reference loading vectors each correspond to one-dimensional function values expressed by the reference OES data.

13. The device of claim 12, wherein the data selector changes and sets the data selection range and outputs the operation control signal whenever further receiving the data selection signal, wherein the OES data operation unit processes, by normalization and PCA, process OES data selected on the basis of the changed data selection range by the data selector and outputs linear process loading vectors during a current process wafer etch or deposition process in response to the operation control signal, and wherein the product generator uses the linear process loading vectors to generate prediction product values from a time of a subsequent process wafer etch or deposition process up to a time of a process wafer etch or deposition process before the OES data operation unit executes a subsequent normalization and PCA process operation.

14. The device of claim 13, wherein the OES data operation unit comprises:

a normalization processor for normalizing the reference OES data and outputting reference average scaling data or normalizing the process OES data and outputting process average scaling data, in response to the operation control signal; and a PCA processor for processing the reference average scaling data by PCA and outputting the linear reference loading vectors or processing the process average scaling data by PCA and outputting the linear process loading vectors.

15. The device of claim 14, wherein the OES data operation unit further comprises: a storage unit for storing the linear reference loading vectors or the linear process loading vectors received from the PCA processor in response to the operation control signal.

16. The device of claim 13, wherein the data selection range is any one or more of at least one set wavelength band range, at least one set time range, and a wavelength band range of lights emitted by at least one set element.

17. A plasma reactor comprising:

a plasma reaction chamber which a reference wafer or a process wafer is mounted inside;

a spectrometer for converting first lights of a whole wavelength emitted from the inside of the plasma reaction chamber into reference OES data during a reference wafer etch or deposition process or converting second lights of a whole wavelength emitted from the inside of the plasma reaction chamber into process OES data during a process wafer etch or deposition process executed after the reference wafer etch or deposition process;

an optical fiber cable for collecting the first or second lights of the whole wavelength emitted from the inside of the plasma reaction chamber through a window provided at an outer wall of the plasma reaction chamber and forwarding the collected lights to the spectrometer during the reference wafer or process wafer etch or deposition process;

an endpoint detection device for detecting a process wafer etch or deposition endpoint and outputting a detection signal on the basis of the reference OES data and the process OES data; and a plasma reaction controller for controlling an etch or deposition condition within the plasma reaction chamber in response to the detection signal, the endpoint detection device comprising:

a data selector for setting a data selection range and outputting an operation control signal in response to a data selection signal, selecting part of reference OES data on the basis of the data selection range during the reference wafer etch or deposition process, and selecting part of process OES data on the basis of the data selection range during the process wafer etch or deposition process;

an OES data operation unit for processing the selected reference OES data by normalization and PCA and outputting linear reference loading vectors in response to the operation control signal;

a product generator for periodically outputting a prediction product value on the basis of the linear reference loading vectors and the selected process OES data; and an endpoint determiner for detecting a process wafer etch or deposition endpoint and outputting a detection signal on the basis of the periodically received prediction product value, wherein the linear reference loading vectors each correspond to one-dimensional function values expressed by the reference OES data.

18. The plasma reactor of claim 17, wherein the data selector changes and sets the data selection range and outputs the operation control signal whenever further receiving the data selection signal, wherein the OES data operation unit processes, by normalization and PCA, process OES data selected on the basis of the changed data selection range by the data selector and outputs linear process loading vectors during a current process wafer etch or deposition process in response to the operation control signal, and wherein the product generator uses the linear process loading vectors to generate prediction product values from a time of a subsequent process wafer etch or deposition process up to a time of a process wafer etch or deposition process before the OES data operation unit executes a subsequent normalization and PCA process operation.

19. The plasma reactor of claim 17, further comprising:

a display unit for displaying the reference OES data or the process OES data in a three-dimensional graphic picture; and an input unit comprising a plurality of keys and outputting the data selection signal in response to pressing the plurality of keys.

* * * * *